United States Patent
Berzak et al.

(10) Patent No.: US 8,636,750 B2
(45) Date of Patent: Jan. 28, 2014

(54) HAIR REMOVAL DEVICE

(75) Inventors: Nir Berzak, Zikhron-Yaakov (IL); Abraham Dayan, Bat-Yam (IL); Yuri Lechtzier, ElAzar (IL); Assaf Guterman, Tel-Aviv (IL); Nir Rotem, Gedera (IL); Uri Amir, Or Yehuda (IL); Alon Goren, Moshav Ben-Shemen (IL)

(73) Assignee: Applisonix Ltd., Rechovot (IL)

( * ) Notice: Subject to any disclaimer, the term of this patent is extended or adjusted under 35 U.S.C. 154(b) by 0 days.

(21) Appl. No.: 13/061,174

(22) PCT Filed: Aug. 27, 2009

(86) PCT No.: PCT/IL2009/000829
§ 371 (c)(1),
(2), (4) Date: May 3, 2011

(87) PCT Pub. No.: WO2010/023667
PCT Pub. Date: Mar. 4, 2010

(65) Prior Publication Data
US 2011/0238085 A1 Sep. 29, 2011
US 2013/0331863 A9 Dec. 12, 2013

Related U.S. Application Data

(63) Continuation-in-part of application No. 12/996,775, filed as application No. PCT/IL2009/000574 on Jun. 9, 2009, said application No. PCT/IL2009/000829 is a continuation-in-part of application No. PCT/IL2009/000574, filed on Jun. 9, 2009.

(60) Provisional application No. 61/136,352, filed on Aug. 29, 2008, provisional application No. 61/129,172, filed on Jun. 9, 2008.

(51) Int. Cl.
*A61B 17/50* (2006.01)

(52) U.S. Cl.
USPC .......................................................... 606/133

(58) Field of Classification Search
USPC .............. 604/22; 606/9, 31, 34, 36, 131, 133, 606/210, 211
See application file for complete search history.

(56) References Cited

U.S. PATENT DOCUMENTS 3,999,552 A 12/1976 Huggins
4,174,713 A 11/1979 Mehl
(Continued)

FOREIGN PATENT DOCUMENTS

CN 1960682 5/2007
EP 0331313 9/1989
(Continued)

OTHER PUBLICATIONS

Translation of Office Action Dated Apr. 16, 2012 From the State Intellectual Property Office of the People's Republic of China Re. Application No. 200980128403.1.

(Continued)

*Primary Examiner* — Ryan Severson
*Assistant Examiner* — Jonathan W Miles

(57) ABSTRACT

A device for removing hair is disclosed. The device comprises a container, filled with an impedance matching medium, and an ultrasound transducer element coupled to the container, such that ultrasound waves are generated by the transducer element in the impedance matching medium. The device further comprises a hair receiving element having at least one opening for receiving hair shafts, wherein a height of the opening is approximately an integer multiplication of half a wavelength of the ultrasound waves.

4 Claims, 16 Drawing Sheets

(56) References Cited

U.S. PATENT DOCUMENTS

| | | | |
|---|---|---|---|
| 4,784,136 A | 11/1988 | Klein | |
| 5,899,900 A | 5/1999 | Burke | |
| 6,139,320 A | 10/2000 | Hahn | |
| 6,436,106 B2 | 8/2002 | Yiu | |
| 6,669,685 B1 | 12/2003 | Rizoiu et al. | |
| RE40,305 E | 5/2008 | Richter | |
| 2002/0036446 A1 | 3/2002 | Toda et al. | |
| 2003/0176791 A1 | 9/2003 | Rabiner et al. | |
| 2006/0027554 A1 | 2/2006 | Hashimoto | |
| 2006/0106375 A1 | 5/2006 | Werneth et al. | |
| 2007/0142714 A1 | 6/2007 | Shumate et al. | |
| 2007/0173746 A1 | 7/2007 | Barzilay et al. | |
| 2007/0276255 A1 | 11/2007 | Leban | |
| 2010/0057097 A1 | 3/2010 | Ma et al. | |
| 2011/0224692 A1* | 9/2011 | Goren et al. | 606/133 |
| 2011/0319795 A1 | 12/2011 | Lechtzier et al. | |

FOREIGN PATENT DOCUMENTS

| | | |
|---|---|---|
| GB | 1513057 | 6/1978 |
| JP | 59-177411 | 11/1984 |
| JP | 10-234459 | 9/1998 |
| JP | 2001-029126 | 2/2001 |
| JP | 2007-522904 | 8/2007 |
| KR | 20020072012 | 9/2002 |
| WO | WO 02/09813 | 0/2002 |
| WO | WO 2005/079687 | 0/2005 |
| WO | WO 2008/024795 | 0/2008 |
| WO | WO 00/21612 | 4/2000 |
| WO | WO 01/26735 | 4/2001 |
| WO | WO 01/33991 | 5/2001 |
| WO | WO 2008/031495 | 3/2008 |
| WO | WO 2008/091625 | 7/2008 |
| WO | WO 2009/150645 | 12/2009 |
| WO | WO 2010/023667 | 3/2010 |
| WO | WO 2010/103508 | 9/2010 |

OTHER PUBLICATIONS

Communication Pursuant to Rules 161(1) and 162 EPC Dated Apr. 11, 2011 From the European Patent Office Re. Application No. 09762170.0.

Response Dated May 8, 2011 to Communication Pursuant to Rules 161(1) and 162 EPC of Apr. 11, 2011 From the European Patent Office Re. Application No. 09762170.0.

International Preliminary Report on Patentability Dated Mar. 10, 2011 From the International Bureau of WIPO Re.: Application No. PCT/IL2009/000829.

International Search Report and the Written Opinion Dated Mar. 3, 2010 From the International Searching Authority Re. Application No. PCT/IL2009/000829.

Official Action Dated Aug. 30, 2012 From the US Patent and Trademark Office Re. U.S. Appl. No. 13/255,243.

International Preliminary Report on Patentability Dated Sep. 22, 2011 From the International Bureau of WIPO Re. Application No. PCT/IL2010/000176.

International Preliminary Report on Patentability Dated Dec. 23, 2010 From the International Bureau of WIPO Re. Application No. PCT/IL2009/000574.

International Search Report and the Written Opinion Dated Jul. 9, 2010 From the International Searching Authority Re.: Application No. PCT/IL2010/000176.

International Search Report and the Written Opinion Dated Nov. 27, 2009 From the International Searching Authority Re.: Application No. PCT/IL2009/000574.

Invitation to Pay Additional Fees Dated Dec. 16, 2009 From the International Searching Authority Re.: Application No. PCT/IL2009/000829.

Second International Search Report and the Written Opinion Dated Jun. 30, 2010 From the International Searching Authority Re.: Application No. PCT/IL2009/000574.

Office Action Dated May 28, 2013 From the Israel Patent Office Re. Application No. 209853 and Its Translation Into English.

Translation of Notice of Reason for Rejection Dated Aug. 13, 2013 From the Japanese Patent Office Re. Application No. 2011-513111.

Office Action Dated Mar. 26, 2013 From the State Intellectual Property Office of the People's Republic of China Re. Application No. 200980142754.8 and Its Summary and Text in English.

Translation of Search Report Dated Mar. 26, 2013 From the State Intellectual Property Office of the People's Republic of China Re. Application No. 200980142754.8.

Official Action Dated Apr. 9, 2013 From the US Patent and Trademark Office Re. U.S. Appl. No. 13/255,243.

Official Action Dated Jan. 22, 2013 From the US Patent and Trademark Office Re. U.S. Appl. No. 12/996,775.

Notice of Reason for Rejection Dated Oct. 25, 2013 From the Japanese Patent Office Re. Application No. 2011-524518 and Its Translation Into English.

* cited by examiner

HAIR REMOVAL DEVICE

RELATED APPLICATION/S

This application is a National Phase of PCT Patent Application No. PCT/IL2009/000829 having International filing date of Aug. 27, 2009, which is a continuation-in-part (CIP) of PCT Patent Application No. PCT/IL2009/000574 having International filing date of Jun. 9, 2009 and which claims the benefit of priority from U.S. Provisional Patent Application No. 61/136,352 filed Aug. 29, 2008. The contents of the above applications are all incorporated herein by reference. This application is also a continuation-in-part (CIP) of U.S. patent application Ser. No. 12/996,775 filed Dec. 8, 2010, which is a National Phase of PCT Patent Application No. PCT/IL2009/000574, which claims the benefit of priority from U.S. Provisional Patent Application No. 61/129,172 filed Jun. 9, 2008.

FIELD AND BACKGROUND OF THE INVENTION

The present invention, in some embodiments thereof, relates to hair removal and, more particularly, but not exclusively, to hair removal by ultrasound.

A hair is composed of a protein named keratin arranged in three layers, termed the outer cuticle, the middle cortex and the central medulla. Hair grows from a follicle, which is a small cup-shaped pit buried under the skin. The walls of the follicle form the outer root sheath of the hair. The base of the hair follicle, called the dermal papilla, is fed by the bloodstream which carries nourishment (e.g., nutrients and oxygen) to produce new hair and removes waste materials formed in the process (e.g., $CO_2$). The lower part of the follicle widens out to form a hair bulb containing a germinal matrix, which is the source of hair growth. Hair growth is initiated in the hair bulge, which is a small swell of the hair follicle that forms the attachment site of a small smooth muscle, called the arrector pili muscle. During the anagen phase (the growing phase of the hair), the dermal papilla sends signals to the stem cells in the hair bulge to migrate downwards along the follicle. Triggered by the dermal papilla, the stem cells begin to proliferate and, following cell differentiation, a new hair shaft is formed.

Various methods and devices exist for removal of undesired hair. Known devices generally pluck hair affixed to a tissue using various types of gripping, pulling and/or cutting means. The existing techniques can be classified into two major categories: short-term and long-term hair removal techniques.

In short-term hair removal techniques, the hair is removed without significantly damaging the biological regeneration and/or re-growth mechanisms found at the base of each hair. Such technique affects only that part of the hair shaft, which is located outside the skin, while the living part of the hair (in the hair follicle attached to dermal papilla) continues to grow. The most common short-term hair removal techniques include: shaving, rotary mechanical epilation, waxing and chemical depilation.

Long-term hair removal techniques affect the biological re-growth mechanisms of the removed hair, and thus have the potential of inhibiting re-growth of unwanted hair from the treated organ. The most common long-term hair removal techniques include: electrolysis, laser and intense pulsed (non-laser) light.

Electrolysis is performed by transmitting a direct current to the hair root in order to form hydroxyl ions that electrochemically destroy the germinative cells of the hair follicles. Electrolysis can also be performed using high frequency currents to heat the water of the hair follicle and to coagulate the germinative hair cells.

U.S. Pat. Nos. 5,632,741 and 5,752,948 disclose methods for hair removal by laser radiation. The hair follicle is irradiated by focused laser beam, resulting in a temperature rise and a destruction of the follicle.

In the intense pulsed light method, filtered light energy is converted in the dermis to heat and absorbed by hair pigment to destroy the hair structures and impair hair re-growth. This method has a much larger spot size than traditional laser technology, hence can cover the treatment area faster and in fewer sessions. On the other hand, in this method, larger areas of the skin are in danger of developing side effects such as thermal injury and pigmentation changes. Some extent of relief to the skin can be provided by extending the duration between successive pulses of light.

U.S. Pat. No. 4,566,454 discloses the application of radiofrequency waves to the hair at a frequency selected such that the hair impedance to radiofrequency energy conduction is substantially lower than at other radiofrequency frequencies. Generally speaking, the main principles of this technique consist of finding and selecting a radiofrequency resonant frequency for a given hair to reduce its impedance, since the resonant frequency varies from hair to hair. Another technique, disclosed in U.S. Pat. No. 5,470,332, consists of a pre-treatment of the hair prior to applying electromagnetic energy thereto. This pre-treatment makes the hair more receptive to the electromagnetic energy prior to its reaching the root of the hair.

International Patent Application Nos. WO 01/13757 and WO 01/033991 disclose hair removal methods in which a hair to be removed is subjected to low frequency vibrations. The low frequency vibrations are transmitted to the hair root either through the hair (WO 01/13757) or by irradiating a treatment zone (WO 01/033991) and exert a force to cause the root to disconnect from the surrounding tissue. The disconnection is mainly due to relatively large vibration amplitude (tens of micrometers to a few millimeters, depending on the vibration generator) of the hair shaft. WO 01/13757 and WO 01/033991 recite a frequency range of four orders of magnitude (10 Hz to 100 kHz), but teach that the preferred vibration frequency is in the sub kilohertz range.

International Patent Publication No. WO 01/26735 discloses a technique for the removal of undesired hair by utilizing ultrasonic resonating waves at a treatment zone in a close proximity to the hair to be removed.

International Patent Publication No. WO 00/21612 discloses a technique for the removal of undesired hair by utilizing ultrasonic forces. The technique involves the production of a focused ultrasonic beam having an acoustic focal point in which the area of the beam is smallest and the intensity of the beam is the highest. The ultrasonic beam is irradiated through the skin, it penetrates through the skin layers above the hair papillae and its focal point reaches the papillae. The parameters of the beam are such that the intensity per unit area on the skin is sufficiently small not to damage the skin above the papillae, while at the focal point the ultrasonic energy is said to be high enough in order to destroy living cells. WO 00/21612 recites a three orders of magnitude range of ultrasound frequencies (20 kHz to 25 MHz), but teaches that the preferred ultrasound frequency is in the range of 3000 kHz to 7000 kHz. WO 00/21612 also teaches generation of cavitations within the hair root, by irradiating using ultrasound waves at a frequency range of 1 kHz to 5 MHz.

International Patent Publication No. WO 02/09813 discloses a hair removal method in which the area from which the hair is to be removed is struck by ultrasonic waves until the temperature of the tissues is raised-as a result of the absorption of the energy carried by the ultrasonic wave-to a degree sufficient to cause damage to the hair follicle. Similarly to WO/0021612 as described hereinabove, WO 02/09813 teaches that the ultrasound waves should be focused, so as to obtain a focal spot with lateral dimensions of order of a few tenths of the millimeter and a longitudinal extension of a few millimeters. The small focal spot has to be precisely directed onto the follicle to cause the desired destruction.

International Patent Publication No. WO 03/065347 discloses a method of treatment of tissue by a focused beam of ultrasonic vibration. WO 03/065347 employs a plano-concave lens which focuses the ultrasonic vibration at the treatment zone.

U.S. Patent Application, Publication No. 2002/0165529 discloses a method of treating subcutaneous tissue to achieve a therapeutic effect of hair removal. The therapeutic effect can be achieved by delivery of ultrasound energy to subsurface tissue. Two or more ultrasound delivery elements are positioned in an array in a manner such that their resulting output constructively interferes and focused onto the desired subsurface location.

International Patent Publication No. WO 99/029245 discloses a method of permanents hair removal method that includes two treating steps. In a first step, ultrasound is used to introduce alkaline ions into the skin and around the hair follicles, and a second step potentiates the destructive chemical reaction between the alkaline ions and the hair follicles, using radiant energy in the visible region.

U.S. Pat. No. 6,544,259 discloses a hair removal method in which radio frequency radiation is applied to a selected skin zone so as to destroy the hair follicles. Subsequently, ultrasound waves are applied to the skin zone to shake up the hair with the destroyed follicle and thus slacken the union between the hair and the skin zone and underlying area. Once the union is slackened the hair is pulled out of the follicle.

U.S. Pat. No. 6,200,326 discloses a method and apparatus for long-term removal of hair by transmitting ultrasound energy to a needle passed through the skin into an individual hair follicle. The resulting cavitations within the area surrounding the hair follicle causes the hair follicle to be disrupted.

International Patent Publication No. WO 2005/079687 discloses a technique in which acoustic waves are transmitted through the hair so as to generate heat at a follicle, a dermal papilla, a hair bulge and/or a germinal matrix of the hair. The heat is in itself sufficient to damage and/or destroy the follicle, the dermal papilla, the hair bulge and/or the germinal matrix.

Additional background art includes Japanese Patent Nos. JP 2001029126 and JP 8154728.

SUMMARY OF THE INVENTION

According to an aspect of some embodiments of the present invention there is provided a device for removing hair. The device comprises a container, filled with an impedance matching medium; an ultrasound transducer element coupled to the container at a first end of the container, such that ultrasound waves are generated by the transducer element in the impedance matching medium; and a hair receiving element at a second end of the container, opposite to the first end, the hair receiving element having at least one opening for receiving hair shafts. In various exemplary embodiments of the invention a height of the at least one opening is approximately an integer multiplication of half a wavelength of the ultrasound waves.

According to some embodiments of the present invention the container is a tubular structure, wherein the receiving element covers the tubular structure at the second end generally perpendicularly to the wall.

According to some embodiments of the present invention the container is a tubular structure, wherein the receiving element is formed as groove in a wall of the tubular structure.

According to some embodiments of the present invention the groove is a linear groove formed generally parallel to a longitudinal axis defined by the tubular structure.

According to some embodiments of the present invention the ultrasound waves are focused to a focus region being at a distance of less than 1 millimeter from the hair receiving element.

According to an aspect of some embodiments of the present invention there is provided a device for removing hair. The device comprises a plurality of tubular transducer elements filled with an impedance matching medium and configured for receiving hair shafts and for generating ultrasound waves in the medium; wherein a height of at least some of the transducer elements is approximately an integer multiplication of half a wavelength of the ultrasound waves.

According to an aspect of some embodiments of the present invention there is provided a device for removing hair. The device comprises a container, filled with an impedance matching medium, and an ultrasound transducer element coupled to the container, such that ultrasound waves are generated by the transducer element in the impedance matching medium, wherein the transducer element is provided at least one opening for receiving hair shafts. According to some embodiments of the present invention a height of the at least one opening is approximately an integer multiplication of half a wavelength of the ultrasound waves.

According to an aspect of some embodiments of the present invention there is provided a device for removing hair. The device comprises a biasing unit and a vibratory unit and having hair-gripping ends biasable towards each other, the biasing unit being configured for receiving hair shafts, and the vibratory unit having an ultrasound transducer element for generating vibrations in a respective hair-gripping end, and at least one elongated vibrating element at the respective hair-gripping end of the vibratory unit, wherein the elongated vibrating element mechanically amplifies an amplitude of the vibrations and transmits the amplified vibrations to the hairs to generate an ultrasound wave therein.

According to some embodiments of the present invention the device further comprises at least one acoustic horn for amplifying vibrations generated by the transducer element and transmitting the amplified vibrations to the elongated vibrating element.

According to some embodiments of the present invention the elongated vibrating element and the acoustic horn are made of the same material.

According to some embodiments of the present invention the elongated vibrating element is an integral extension of the acoustic horn.

According to some embodiments of the present invention the device further comprises supporting arms for fixing preventing or reducing vibrations at the ends of the vibrating element but allowing vibrations at a central portion thereof.

According to some embodiments of the present invention the device further comprises a clamping member for applying a pre-load force on the transducer element to increase displacement thereof.

According to some embodiments of the present invention the biasing unit comprises a slanted surface for raising a plurality of hair shafts from a skin of a subject onto the surface.

According to some embodiments of the present invention the biasing unit comprises at least one opening for receiving the hair shafts.

According to an aspect of some embodiments of the present invention there is provided a device for removing hair. The device comprises an ultrasound piezoelectric film for generating vibrations, a hair receiving element having at least one opening for receiving hair shafts, and a pressure plate configured for applying pressure on the piezoelectric film so as to bias the piezoelectric film on the hair shafts and to allow the piezoelectric film to transmit the vibrations to the hair shafts to generate ultrasound waves therein. According to some embodiments of the present invention the piezoelectric film is flexible.

According to an aspect of some embodiments of the present invention there is provided a device for removing hair. The device comprises: a vibratory unit for generating vibrations and a biasing unit for biasing the vibratory unit, each of the vibratory unit and the biasing unit having a disk with a plurality of wings arranged on a periphery of the disk, the vibratory unit and the biasing unit being operatively connected in a rotatable manner such that wings of the vibratory unit are interlaced with wings of the biasing unit, wherein a rotary motion of at least one of the units grips hair shafts between the wings of the biasing unit and the wings of the vibratory unit. According to some embodiments of the present invention the vibratory unit further comprises an ultrasound transducer element coupled to the disk.

According to some embodiments of the present invention the device further comprises an acoustic horn for amplifying vibrations generated by the transducer element and transmitting the amplified vibrations to the disk.

According to some embodiments of the present invention the disk of the vibratory unit is an ultrasound transducer element.

According to some embodiments of the present invention for at least one of the units, the respective wings are integral extensions of the respective disk.

According to an aspect of some embodiments of the present invention there is provided a device for removing hair. The device comprises a first unit having a first unit body and a bulge, outwardly protruding from the unit body, the first unit being coupled to an ultrasound transducer element for vibrating the first unit body; and a second unit having a second unit body formed with recess being shape-wise compatible to the bulge; wherein the first and the second units are biasable towards each other such that when the bulge engagers the recess, hair shafts are griped between the bulge and the recess and are vibrated by vibratory motion of at least the first unit body.

According to some embodiments of the present invention the transducer element is positioned in a recess formed within the first unit body.

According to some embodiments of the present invention the engagement establishes a direct contact between the hair shafts and the transducer element.

According to some embodiments of the present invention the engagement is such as to avoid a direct contact between the hair shafts and the transducer element.

According to an aspect of some embodiments of the present invention there is provided a device for removing hair. The device comprises a flexible vibratory unit and a flexible biasing unit, both being shaped as spiral sheets wound one around the other, the vibratory unit having an ultrasound transducer element attached to or integrated with the respective sheet, the sheets being configured to receive hair shafts in a spiral spacing between the sheets, and to establish a spiral motion with respect to each other so as to tighten the spacing to thereby grip the hair shafts. Vibratory motion of the transducer element is transferred by the sheets to the hair shafts to generate ultrasound wave therein.

According to an aspect of some embodiments of the present invention there is provided a device for removing hair. The device comprises a vibratory unit having an ultrasound transducer element, a vibrating element and an acoustic horn between the transducer element and the vibrating element, wherein vibratory motion of the transducer element is transferred by the horn to the vibrating element; and a biasing unit having a gripping element and an actuator mechanism configured for closing and opening the gripping element onto the vibrating element. The actuator mechanism is operative to establish a linear motion of the gripping element along the horn such that a linear motion along a first direction opens a gap between the gripping element and the vibrating element to receive hair shafts in the gap, and a linear motion along a second direction, opposite to the first direction, closes the gripping element on the vibrating element so as to grip the hairs therebetween and to transfer the vibratory motion to the hair shafts for generating ultrasound wave therein.

According to some embodiments of the present invention the device further comprises a hair raising mechanism configured for raising the hair shafts from a skin of a subject to facilitate entry of the hair shafts to the device.

According to an aspect of some embodiments of the present invention there is provided a method of removing hair. The method comprises entering hair shafts the device according to any of the embodiments described herein and energizing the transducer element, at a frequency selected such as to generate an ultrasound wave in the hair shafts, wherein an acoustic energy of the ultrasound wave generates a sufficient amount of heat at the hair's root to at least damage the follicle, dermal papilla, hair bulge and/or germinal matrix.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
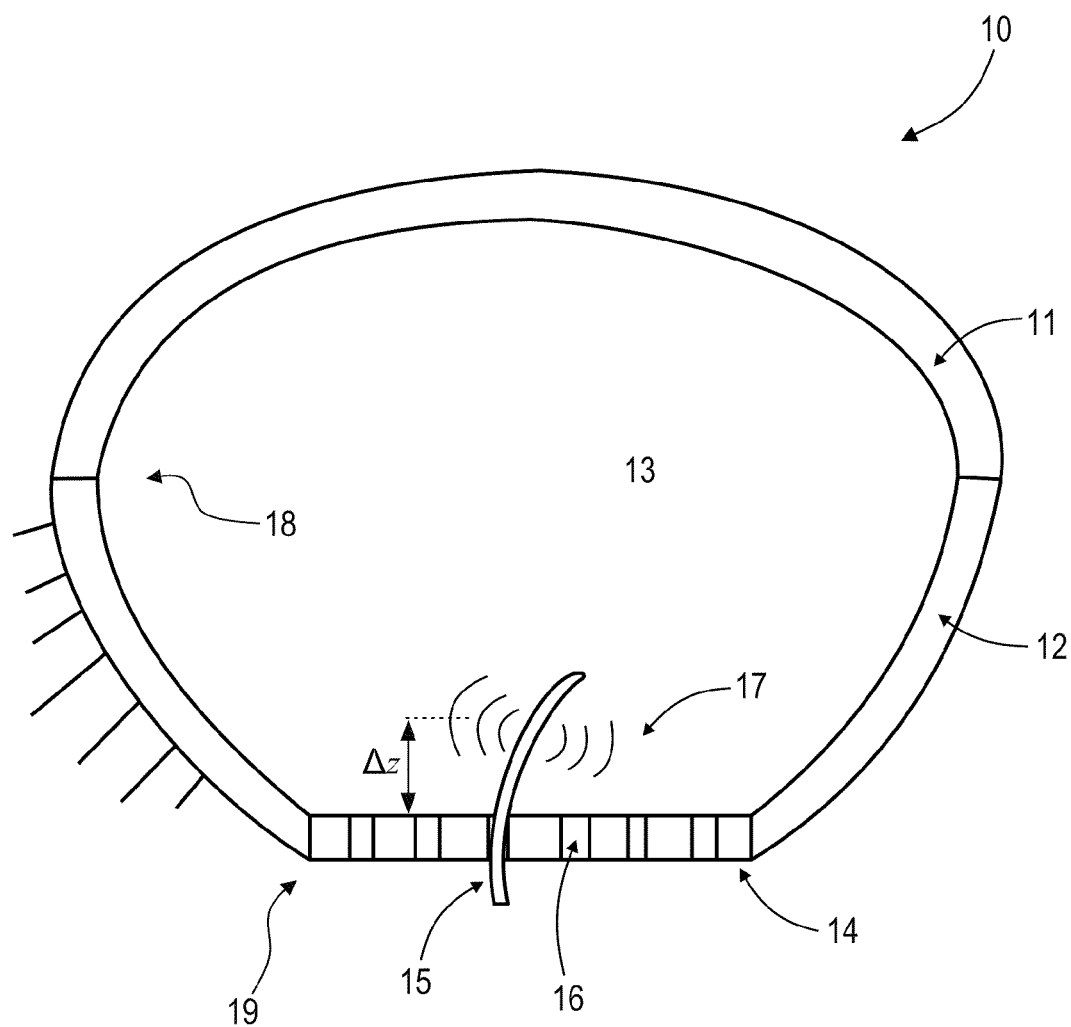
FIG. 1 is a schematic illustration of a device for removing hair according to some embodiments of the present invention.

The present invention, in some embodiments thereof, relates to hair removal and, more particularly, but not exclusively, to hair removal by ultrasound.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present embodiments utilize the hair shaft as an acoustic energy carrier, for the purpose of treating unwanted hair. The acoustic energy generates a sufficient amount of heat at the hair's root such that that the root is destroyed or at least damaged by the heat.

As used herein, destruction of hair's root refers to hyperthermia, necrosis and/or any other damage to the cells in the follicle (dermal papilla, hair bulge, germinal matrix, etc.) which, at least temporarily, preferably permanently prevents the re-growth of the hair. The prevention of re-growth is preferably for a prolonged period of time, for example, for more than a month, preferably for more than six months, more preferably for more than a year, most preferably permanently.

When the temperature of the soft tissue present in the follicle reaches high levels for a sufficient duration, a phenomenon known as "protein denaturing" can occur, resulting in a necrosis of the tissue. The heat generated by the acoustic energy at the root can result in a temperature increment of at least 20° C., or at least 30° C., or at least 40° C. Such heat in itself is sufficient to at least temporarily, preferably permanently destroy or at least damage the follicle, dermal papilla, hair bulge and/or germinal matrix.

The use of the hair shaft as an acoustic energy carrier reduces or eliminate the sensitivity of the treatment to several physiological parameters of the treated person, such as, but not limited to, skin color tone, hair color tone and level of contrast between skin color tone and hair color tone. Prior art hair removal techniques making use of other energy types (e.g., light, laser, electromagnetic radiation, radiofrequency radiation, X-ray radiation) are significantly sensitive to such color tone parameters. Thus, the present embodiments have the advantage of treating significantly larger populations comparing with such other hair removal techniques. Without limitation, the present embodiments are suitable for individuals with dark skin tone, individuals with very light hair tone, and individuals with minimal amount of melanin in the hair.

The present embodiments take advantage of the proximity of the dermal papilla, hair bulge and germinal matrix to the hair shaft. In particular, this proximity is exploited during the hair Anagen growth phase, whereby acoustic energy carried by the hair shaft, is converted into thermal energy in the follicle, dermal papilla, hair bulge and germinal matrix. When integrated within the hair base, and taking into account the very small volume of the dermal papilla, hair bulge and germinal matrix (several hundreds of cubic microns), a rapid and short increase in the temperature as a result of absorption of acoustic energy, timely elevates the generation of sufficient thermal effects, sufficient enough to cause the desired destruction of cells. Preferably, the thermal effects are sufficiently short in their duration, so as to selectively destroy the follicle, germinal matrix, hair bulge and/or dermal papilla, with minimal or no damage to other soft biological tissues surrounding the follicle or hair shaft. The combination of short duration and use of the hair shaft as an acoustic energy carrier allows the selective damage to the cells in the follicle substantially without damaging other important tissues and sub-organs surrounding the hair shaft and bulb.

The parameters of the acoustic waves may be adapted according to one or more of the following physiological parameters characterizing the person and/or body organ being treated: hair growth phase (Anagen, Catagen or Telogen), depth of the hair base under the skin, distance between hair base and papilla, total hair length (under and above the skin), hair coupling angle, hair color, hair diameter, force required to detach a vital untreated hair from vital untreated hair base, force required to detach a hair from a partially treated hair base, and force required to detach a hair from fully treated and materially destroyed hair base.

Referring now to the drawings, FIG. 1 illustrates a device 10 for removing hair according to some embodiments of the present invention. Device 10 comprises container 12, filled with an impedance matching medium 13, such as an ultrasonic gel or the like. An ultrasound transducer element 11, e.g., a piezoelectric element, is coupled to a container 12 at one of its ends, referred to as the proximal end 18, such that ultrasound waves are generated by transducer element 11 in medium 13. Transducer element 11 can be planar or it can have a curvature, as desired. Container 12 preferably has a curved shape selected to focus the ultrasound waves to a focus region 17 of high acoustic pressure, at a distance Δz from an end 19 of container 12 which is distal with respect to element 11.

For example, container can have a shape of a tapered frustum (e.g., conical frustum, pyramidal frustum) having a large-area base and a small-area base, wherein transducer element 11 is coupled to the large-area base of the frustum. Focus region 17 may be a focal spot but, more preferably, focus region 17 is a locus of focal spots of ultrasound energy. For example, focus region 17 may be a substantially planar locus at some distance from transducer element 11.

In various exemplary embodiments of the invention device 10 comprises a hair receiving element 14 covering container 12 at end 19. When container 12 is shaped as a tapered frustum, element 14 preferably covers the small-area base of the frustum. Element 14 can have a generally planar shape or it can have some curvature as desired. Element 14 comprises one or more openings 16 formed as necks in the body of hair receiving element 14, and constituted to receive one or more hair shafts 15 such that the upper part of the hair shafts enters the volume encapsulated by container 12 and contacts medium 13.

It was found by the present Inventors that focus region 17 can be formed in close proximity to element 14 when the height of necks 16 is approximately an integer multiplication of half the wavelength of the ultrasound wave generated by element 11. Such neck is referred to herein as "resonant neck." In various exemplary embodiments of the invention the height of necks 16 is approximately λ/2, where λ is the wavelength of the ultrasound wave. In some embodiments of the present invention the height of necks 16 is approximately λ, and in some embodiments the height of necks 16 is approximately 1.5λ. In such construction, a standing wave is formed within necks 16 and focus region 17 is formed near necks 16. The hair shafts pass through focus region 17 and the high pressure at region 17 induces in the hair shafts longitudinal ultrasound waves which generate heat at the root of the hair (not shown) as further detailed hereinabove.

Necks 16 can be of any tubular shape, including, without limitation, cylindrical necks. In various exemplary embodiments of the invention the diameter of the necks is substantially smaller than the wavelength of the ultrasound wave.

Figure 2:
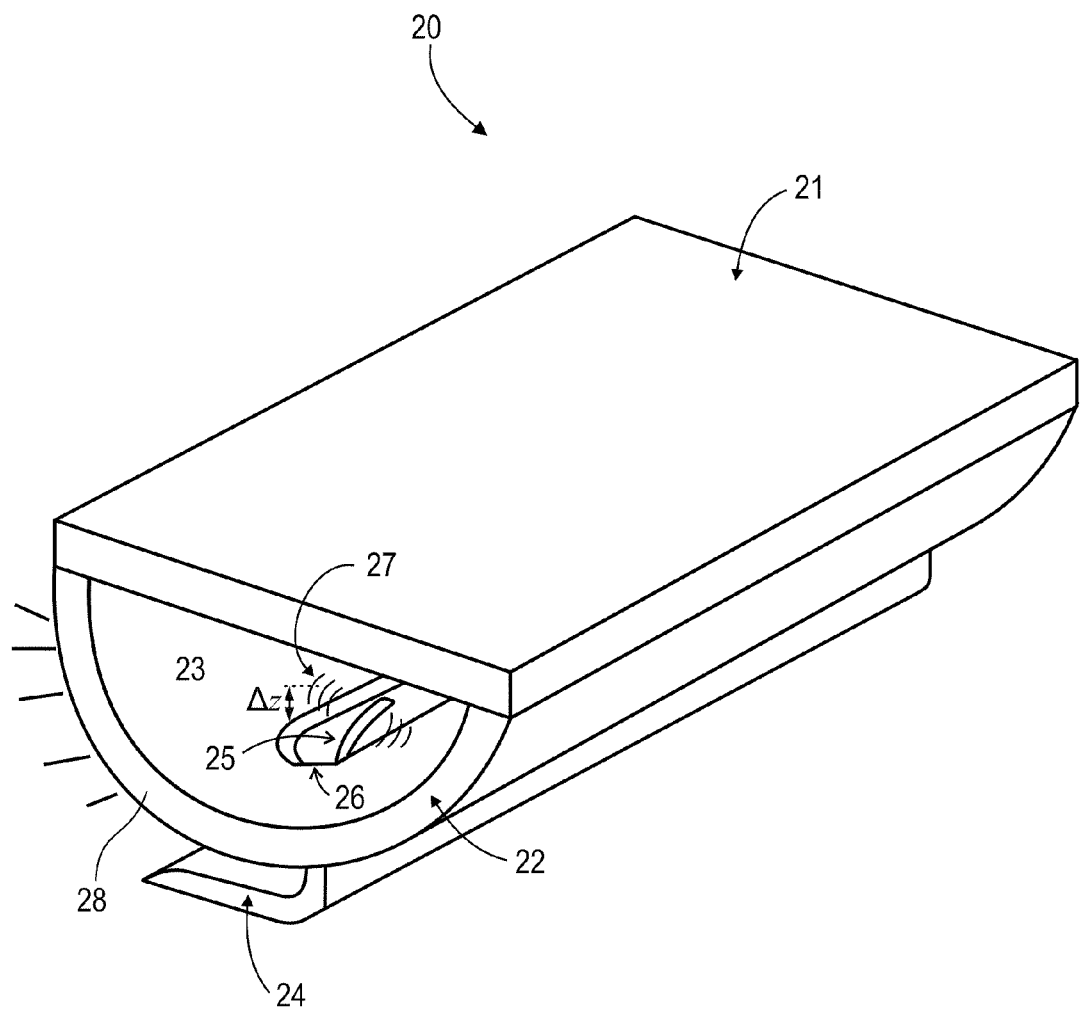
FIG. 2 is a schematic illustration of a device for removing hair in embodiments of the invention in which the device comprises a slot through which hair shafts enter the device.

FIG. 2 is a schematic illustration of a device 20 for removing hair according to some embodiments of the present invention. Device 20 is a variant of device 10, in that it further comprises a mechanism 24 that raises hair shafts from the skin and into device 20. Similarly to device 10, device 20 comprises an ultrasound transducer element 21, e.g., a piezoelectric element, and a container 22 filled with an impedance matching medium 23, which can operate generally as described above with respect to device 10. In the schematic illustration of FIG. 2, container 22 is generally half a cylinder and it is provided with an opening 26 shaped, e.g., as a linear groove formed in the wall 28 of container 22 generally parallel to the symmetry axis of the cylinder. However, this need not necessarily be the case, since, for some applications, it may not be necessary for opening 26 to be shaped as a linear groove. For example, openings 26 can be a plurality of ports, such as cylindrical holes, or the like.

Transducer element 21 is coupled to container 22 such that ultrasound waves are generated by transducer element 21 in medium 23. The ultrasound waves are focused to a focus region 27 of high acoustic pressure, at a distance Δz from the inwardly facing end of opening(s) 26.

Opening(s) 26 preferably receive a plurality of hair shafts. However, for clarity of presentation only one hair shaft is shown at 25. The thickness of the wall 28 of container 22 (hence also the height of opening(s) 26) is optionally about an integer multiplication of half the wavelength of the ultrasound wave generated by element 21. Thus, in these embodiments opening(s) 26 are resonant necks. In various exemplary embodiments of the invention the height of opening(s) 26 is approximately λ/2, where λ is the wavelength of the ultrasound wave. In some embodiments of the present invention the height of opening(s) 26 is approximately λ, and in some embodiments the height of opening(s) 26 is approximately 1.5λ. It was found by the present inventor that such construction allows generation of a focus region 27 within container 22 but in proximity to opening(s) 26 so as to allow hair shafts 25 to pass through region 27 wherein the high pressure at region 27 induces in the hair shafts longitudinal ultrasound waves which generate heat at the root of the hairs as further detailed hereinabove.

Opening(s) 26 can be of any tubular shape, including, without limitation, cylindrical necks. In various exemplary embodiments of the invention the diameter of the openings is substantially smaller than the wavelength of the ultrasound wave.

Figure 3:
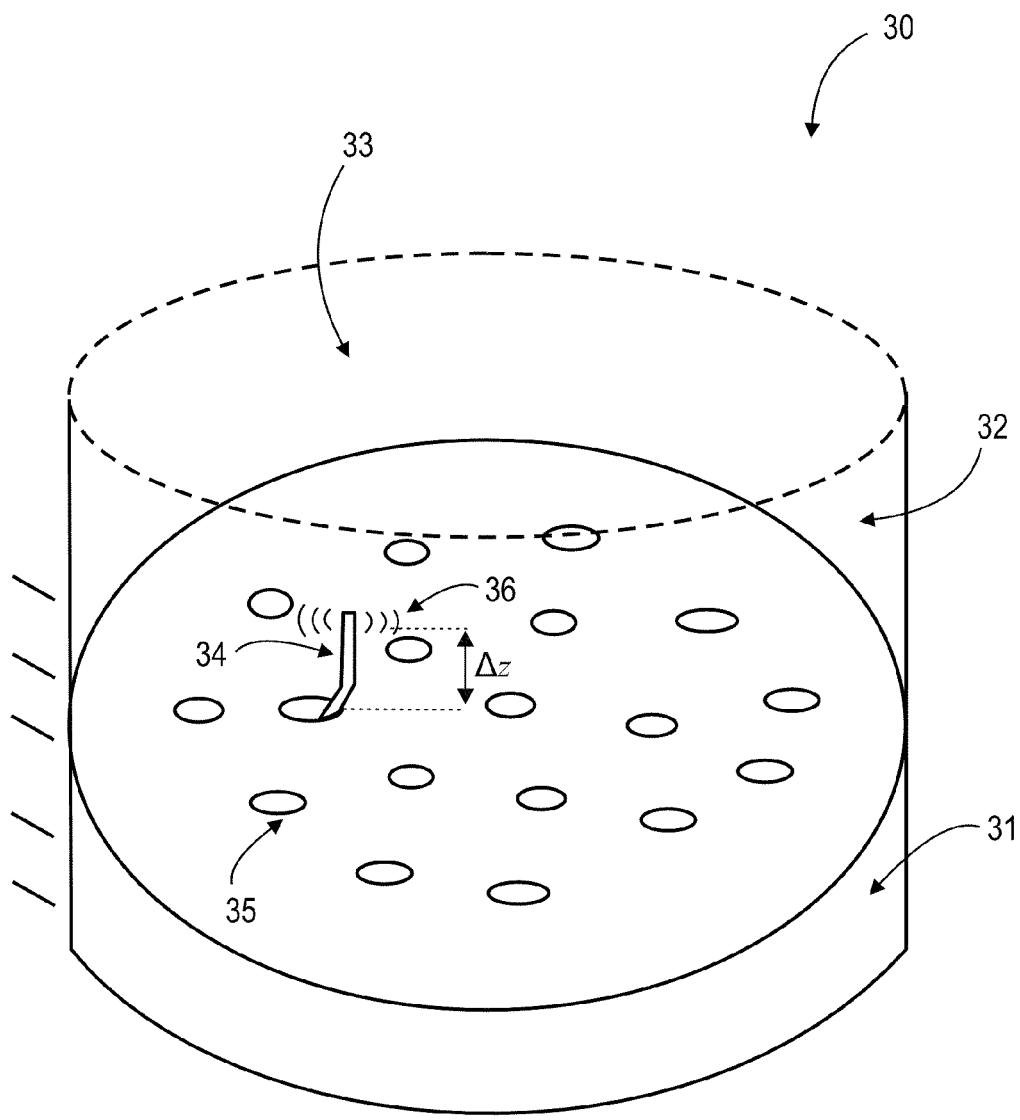
FIG. 3 is a schematic illustration of a device for removing hair in embodiments of the invention in which the device comprises an ultrasound transducer element having one or more openings

FIG. 3 is a schematic illustration of a device 30 for removing hair according to some embodiments of the present invention. Device 30 is a variant of device 10, in that it comprises an ultrasound transducer element 31, e.g., a piezoelectric element, which is provided with one or more openings 35 formed as necks in the body of transducer element. Similarly to device 10, device 30 further comprises a container 32 filled with an impedance matching medium 33. The operation of device 30 is similar to the operation of device 10, except that a focus region 36 of high acoustic pressure is preferably formed near openings 35 of element 31 (namely near the proximal end of the container rather than near the distal end). Focus region 36 is formed at a distance Δz from the inwardly facing end of opening(s) 35.

In various exemplary embodiments of the invention the height of openings 35 is approximately an integer multiplication of half the wavelength of the ultrasound wave generated by element 31. In various exemplary embodiments of the invention the height of openings 35 is approximately λ/2, where λ is the wavelength of the ultrasound wave. In some embodiments of the present invention the height of openings 35 is approximately λ, and in some embodiments the height of openings 35 is approximately 1.5λ. Openings 35 receive hair shafts 34 which preferably pass through focus region 36 wherein the high pressure at region 36 induces in the hair shafts longitudinal ultrasound waves which generate heat at the root of the hairs as further detailed hereinabove.

Opening(s) 35 can be of any tubular shape, including, without limitation, cylindrical necks. In various exemplary embodiments of the invention the diameter of the openings is substantially smaller than the wavelength of the ultrasound wave.

Figure 4:
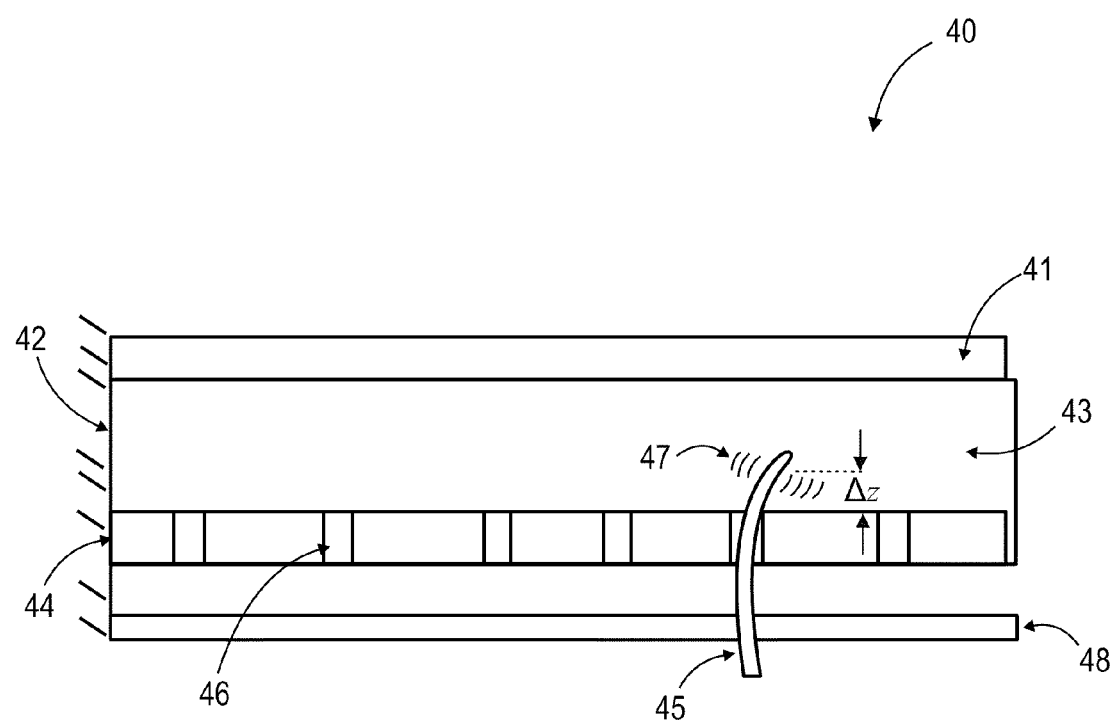
FIG. 4 is a schematic illustration of a device for removing hair in embodiments of the invention in which the device comprises a mechanism which directs the hairs into device.

FIG. 4 is a schematic illustration of a device 40 for removing hair according to some embodiments of the present invention. Device 40 is a variant of device 10, in that it further comprises a mechanism 48 which directs the hairs into device 40. Mechanism 48 can be a perforated plate or a comb or any other device suitable for lifting the hair shafts off the skin. Similarly to device 10, device 40 comprises an ultrasound transducer element 41, e.g., a piezoelectric element, a container 42 filled with an impedance matching medium 43 and a hair receiving element 44 covering container 42 at an end which is distal with respect to element 41. Element 44 can have a generally planar shape or it can have some curvature as desired. Element 44 comprises one or more openings 46 formed as necks in the body of hair receiving element 44, and constituted to receive one or more hair shafts 45 such that the upper part of the hair shafts enters the volume encapsulated by container 42 and contacts medium 43.

The principle and operation of device 40 is generally the same as described above with respect to device 10, except that the hair shafts are lifted by mechanism 48 and enter openings 46. A focus region 47 of high acoustic pressure is formed at a distance Δz from the inwardly facing end of opening(s) 46. Preferably, focus region 47 is formed in close proximity to element 44 to allow exposing the hair shaft to the high acoustic pressure. This can be achieved by providing element 44 with necks 46 having a height of approximately an integer multiplication of half the wavelength of the ultrasound wave generated by element 41. Thus, in these embodiments necks 46 are resonant necks. In various exemplary embodiments of the invention the height of necks 46 is approximately λ/2, where λ is the wavelength of the ultrasound wave. In some embodiments of the present invention the height of necks 46 is approximately λ, and in some embodiments the height of necks 46 is approximately 1.5λ.

Necks 46 can be of any tubular shape, including, without limitation, cylindrical necks. In various exemplary embodiments of the invention the diameter of the necks is substantially smaller than the wavelength of the ultrasound wave.

Figure 16:
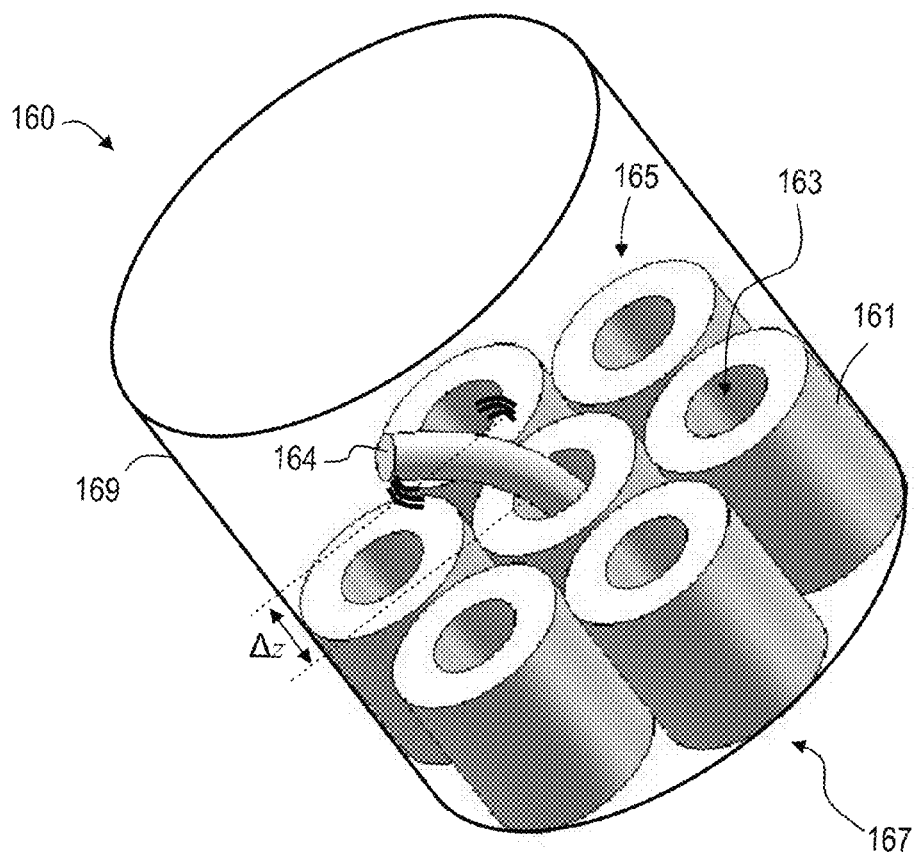
FIG. 16 is a schematic illustration of a device for removing hair in embodiments of the invention in which the device comprises a plurality of tubular transducer elements.

FIG. 16 is a schematic illustration of a device 160 for removing hair according to some embodiments of the present invention. Device 160 comprises a plurality of tubular (e.g., cylindrical) ultrasound transducer elements 161, e.g., piezoelectric elements, filled with an impedance matching medium 163, such as an ultrasonic gel or the like. In various exemplary embodiments of the invention the inner diameter of transducer elements 161 is substantially smaller than the wavelength of the ultrasound wave generated by transducer elements 161.

In use, tubular transducer elements 161 receive hair shafts 164 from a first end 167 of elements 161 and are energized to generate ultrasound waves in medium 163. In various exemplary embodiments of the invention device 160 further comprising a container 169 coupled to transducer elements 161 such that at least a second end 165 of elements 161 is encapsulated by container 169. In this embodiments hair shafts 164 protrude out of ends 165 into container 169. Container 169 can have any shape. Preferably, the shape of container 169 is selected such that when elements 161 are activated, focal spots of high acoustic pressures are generated within the cavity of the container.

In various exemplary embodiments of the invention the height of tubular transducer elements 161 is approximately an integer multiplication of half the wavelength of the ultrasound wave generated thereby. Thus, in these embodiments, tubular transducer elements 161 is a resonant transducer element. In various exemplary embodiments of the invention the height of elements 161 is approximately λ/2, where λ is the wavelength of the ultrasound wave. In some embodiments of the present invention the height of elements 161 is approximately λ, and in some embodiments the height of elements 161 is approximately 1.5λ. It was found by the present inventor that this construction generates a focus region 162 at a distance Δz from ends 165 and sufficiently close thereto, optionally and preferably within container 169, such that the high pressure at the focus region induces in the hair shafts longitudinal ultrasound waves which generate heat at the root of the hairs as further detailed hereinabove.

In any of the above embodiments, the ultrasound transducer element preferably vibrates at an ultrasound frequency of from about 500 kHz to about 2 MHz. In any of the above embodiments, the focused region of high acoustic pressure is formed at a distance Δz of less than 1 mm, more preferably less than 0.75 mm, more preferably less than 0.50 mm, more preferably less than 0.25 mm, from the inwardly facing end of the opening which receives the hair shafts.

Following is a description of various embodiments in which the ultrasound wave is generated in the hair shaft by direct vibration of the hair shaft.

Figure 5:
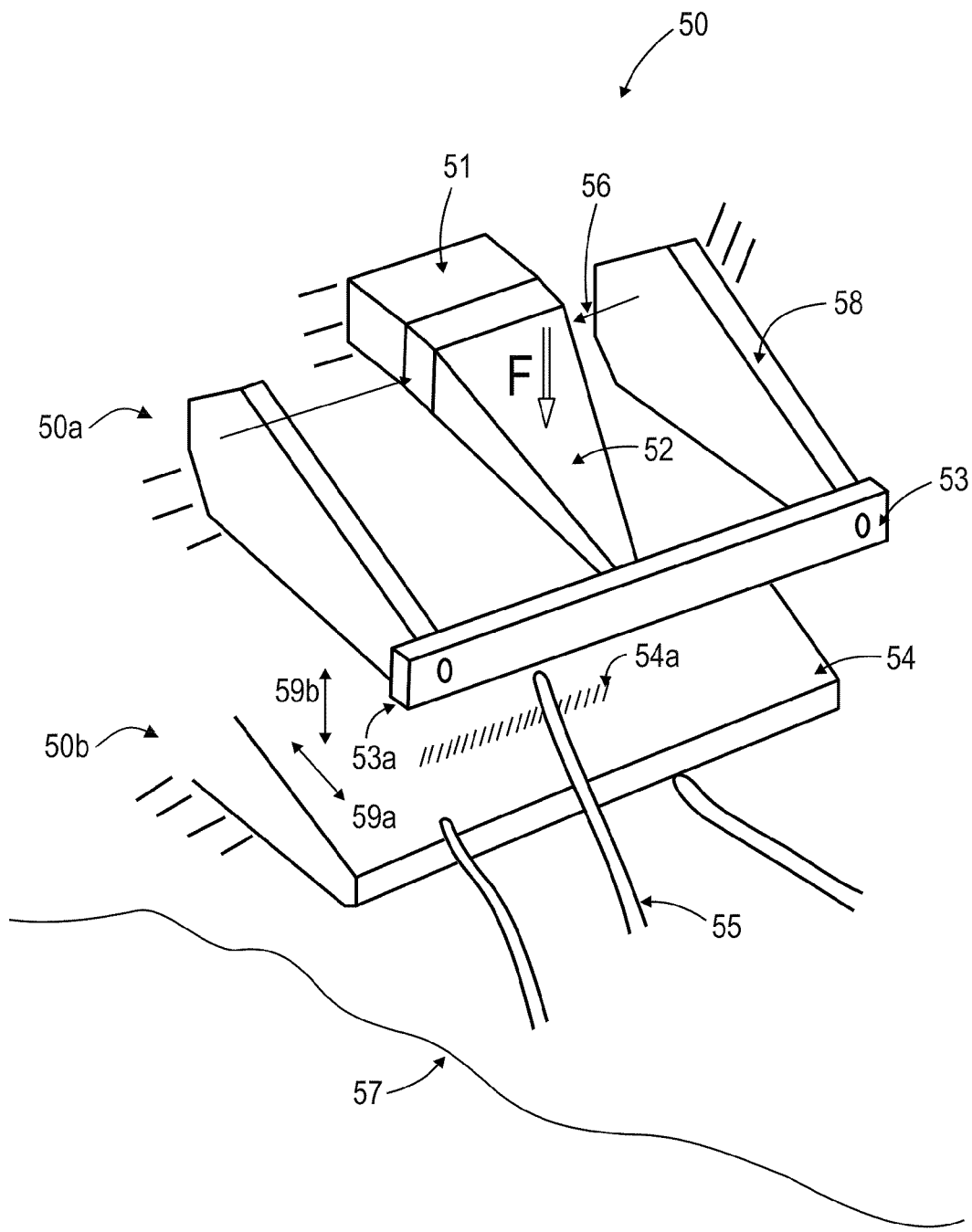
FIG. 5 is a schematic illustration of a device for removing hair in embodiments of the invention in which an ultrasound wave is coupled into the hair shaft by direct vibration, according to some embodiments of the present invention.

One example of such embodiment is illustrated in FIG. 5. Shown in FIG. 5 is a device 50 for directly vibrating hair so as to generate an acoustic wave in the hair and to heat the root of the hair. Device 50 generally comprises a vibratory unit or tong 50a and a biasing unit or tong 50b. Tong 50a serves as a "hammer" and is mounted in a cantilever fashion. This tong can include an ultrasound transducer element 51, e.g., a piezoelectric element, a horn 52, supporting arms 58 and an elongated vibrating element 53. Horn 52 is constructed to receive vibrations from transducer element 51, and transmit the vibrations to vibrating element 53. Preferably, horn 52 is tapered toward vibrating element 53 so as to multiply the vibrations. In some embodiments, horn 52 is a stepped horn as known in the art. Supporting arms 58 can be fixed to the ends of element 53 so as to maintain maximal vibratory amplitude at the center of element 53.

Tong 50b of device 50, serves as an "anvil" and can have the shape of a slanted planar surface 54, which lifts hair shafts 55 off the skin surface 57.

In operation, the two tongs are pressed against each other and the hair is gripped between a contact surface 53a of auxiliary vibrating element 53, and a contact surface 54a of planar surface 54. The two tongs are pre-stressed loaded by a force, shown by arrow F, biasing the two inturned surfaces 53a and 54a towards each other. When element 51 is activated, vibrations are transmitted through horn 52 to vibrating element 53 which in turn transmits the vibrations to the hair shaft. These vibrations generate a longitudinal ultrasound wave in the hair shaft, which ultrasound wave generates heat at the root as further detailed hereinabove.

Transducer element 51 may be constructed so as to induce vibratory displacements of element 53 along the longitudinal axis of the hair, as shown by arrow 59a, or perpendicularly to the hair, as shown by arrow 59b. Also contemplated, are vibratory motions which are a combination of motion along the longitudinal axis of the hair and motion perpendicularly to the hair.

Figure 6:
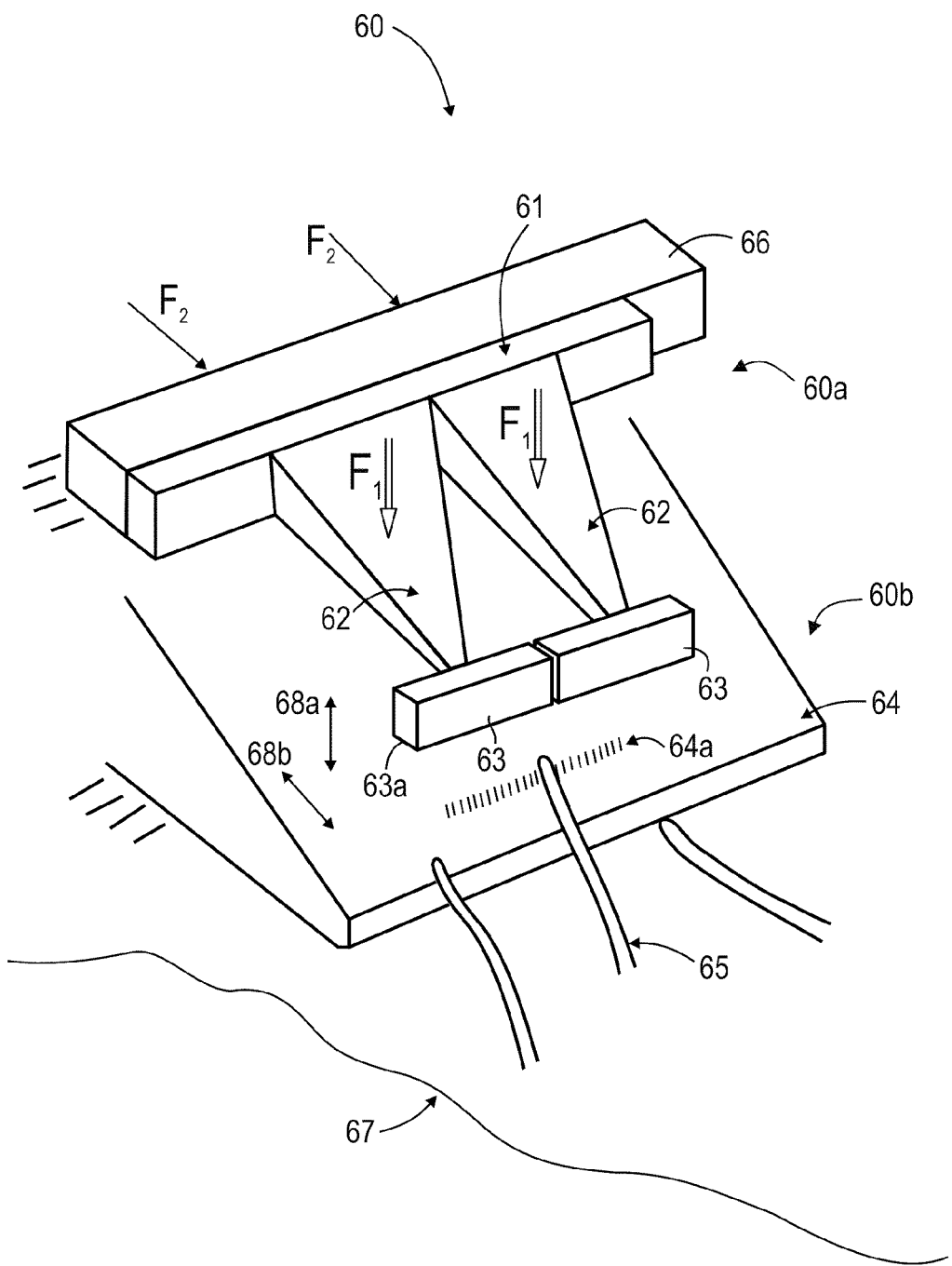
FIG. 6 is a schematic illustration of a device for removing hair in embodiments of the invention in which the device comprises a clamping member.

FIG. 6 illustrates a device 60 which is a variant of device 50 in that device 60 further comprises a clamping member 66 for applying a pre-load force $F_2$. Device 60 comprises a vibratory unit or tong 60a serving as a "hammer", and a biasing unit or tong 60b serving as an "anvil". Vibratory tong 60a includes an ultrasound transducer element 61, e.g., a piezoelectric element, one or more horns 62 and one or more vibrating elements 63 connected to or being an integral part of horns 62. Biasing tong 60b can have the shape of a slanted planar surface 64 similarly to tong 50b described above.

Preferably, horn 62 is tapered toward vibrating element 53 so as to multiply the vibrations. In some embodiments, horn 62 is a stepped horn as known in the art. Optionally and preferably, the amplitude of the vibrations are further amplified by the vibrating element 63. This can be done, for example, by providing vibrating element 63 with sufficient flexibility and elasticity such that the amplitude of the vibrations is enhanced by an elastic resonance effect. Thus, in various exemplary embodiments of the invention the amplitude of the vibratory displacement at the ends of element 63 are X times larger than the amplitude of the vibratory displacement at the contact between horn 62 and element 63, where X is can be any positive number larger than 1, e.g., at least 1.5, more preferably at least 2, more preferably at least 4, more preferably at least 6, more preferably at least 8, more preferably at least 10.

In operation, biasing tong 60b lifts hair shafts shown at 65, from the skin surface 67 onto surface 64 and the two tongs are pressed against each other by force $F_1$ so as to grip the hair between a contact surface 63a of vibrating element 63 and a contact surface 64a of tong 64. Transducer element 61 may be constructed so as to induce vibratory displacements of element 63 along the longitudinal axis of the hair, as shown by arrow 68a, or perpendicularly to the hair, as shown by arrow 68b. Also contemplated, are vibratory motions which are a combination of motion along the longitudinal axis of the hair and motion perpendicularly to the hair. The force $F_2$ applied by clamping member 66 increases the displacement of transducer element 61 in the vibration direction 68a or 68b.

Figure 7:
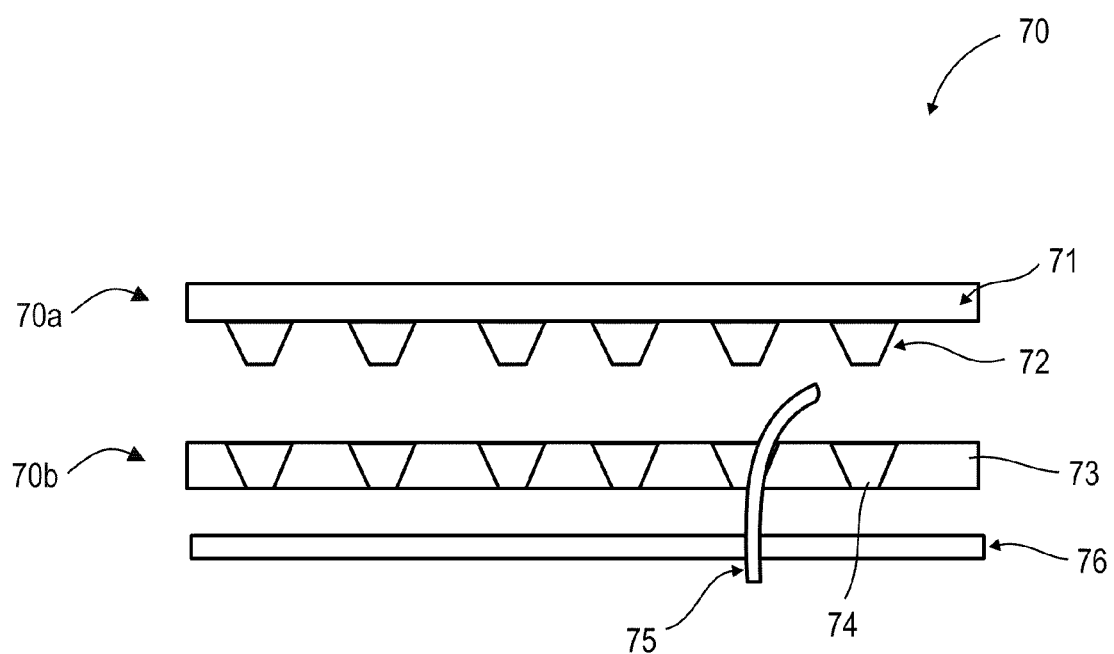
FIG. 7 is a schematic illustration of a device for removing hair in embodiments of the invention in which the hairs enter the device via openings formed in a tong of the device, according to some embodiments of the present invention.

FIG. 7 illustrates a device 70 which is a variant of device 50 in that in device 70 the hairs enter the device via openings formed in one of the units. Device 70 comprises a vibratory unit 70a and a biasing unit 70b. Vibratory unit 70a includes an ultrasound transducer element 71, e.g., a piezoelectric element, and one or more horns 72, and biasing unit 70b includes a plate 73 formed with a plurality of openings 74 for receiving hairs 75 therethrough. Openings 74 are preferably shape-wise compatible to horns 72 such that units 70a and 70b form plug-socket pair wherein each of horns 72 fits into one of openings 74.

In various exemplary embodiments of the invention device 70 further comprises a hair raising mechanism 76 which raises the hair shafts from the skin and into device 70. Mechanism 76 can be a perforated plate or a comb or any other device suitable for lifting the hair shafts off the skin. In use, the hairs are lifted off the skin and enter openings 74. Units 70a and 70b are pressed against each other such that the horns 72 enter openings 74 in a plug-socket relationship. Thus, horns 72 contact the hairs and transmit mechanical vibration which results in longitudinal ultrasound wave along the axes of the hair shafts.

Figure 8:
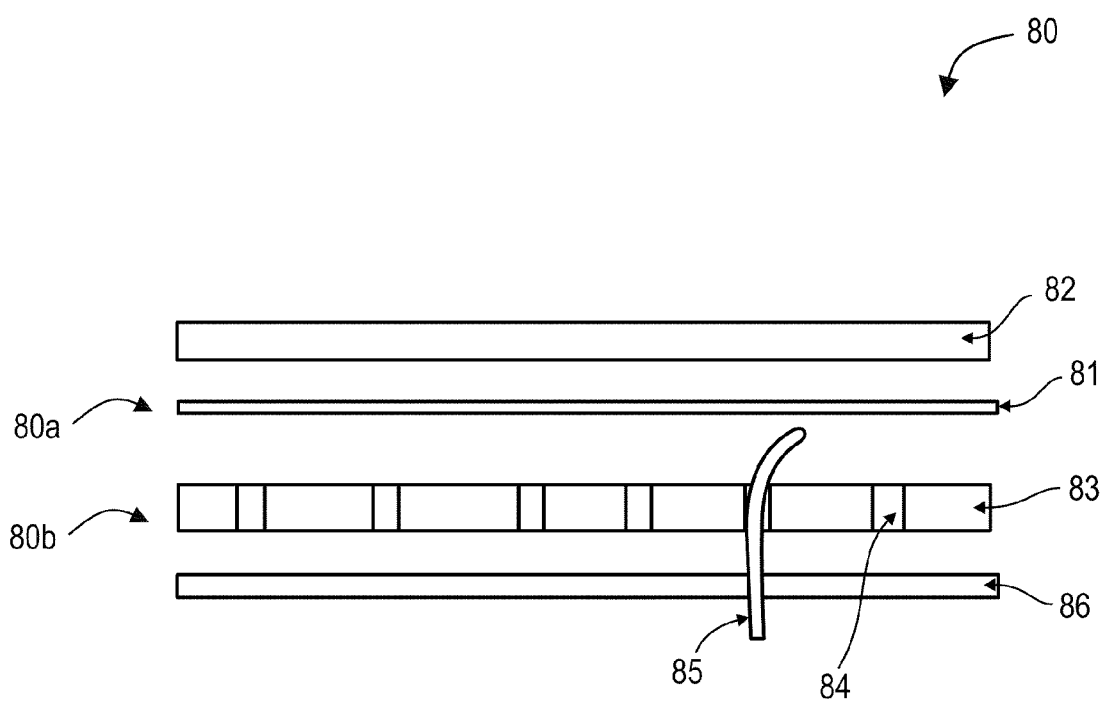
FIG. 8 is a schematic illustration of a device for removing hair in embodiments of the invention in which the device comprises an ultrasound piezoelectric film, according to various exemplary embodiments of the present invention.

FIG. 8 illustrates a device 80 which is a variant of device 70 in that in device 80 the transducer element is a piezoelectric film. Similarly to device 70, device 80 comprises a vibratory unit 80a and biasing unit 80b. Vibratory unit 80a includes a piezoelectric film 81 which can be a flexible piezoelectric film and a pressure plate 82 which applies pressure on film 81. Biasing unit 80b includes a plate 83 formed with a plurality of openings 84 for receiving hairs 85 therethrough, and is generally similar to biasing unit 70b of device 70. In various exemplary embodiments of the invention device 80 further comprises a hair raising mechanism 86 which can be similar to mechanism 76 as further detailed hereinabove. In use, the units are pressed against each other such that pressure plate 82 applies pressure on film 81 hence also on hairs 85 which are pressed between plate 83 and film 81. The pressure applied by plate 82 allows film 81 to transfer the vibrations to hairs 85.

Figure 9A:
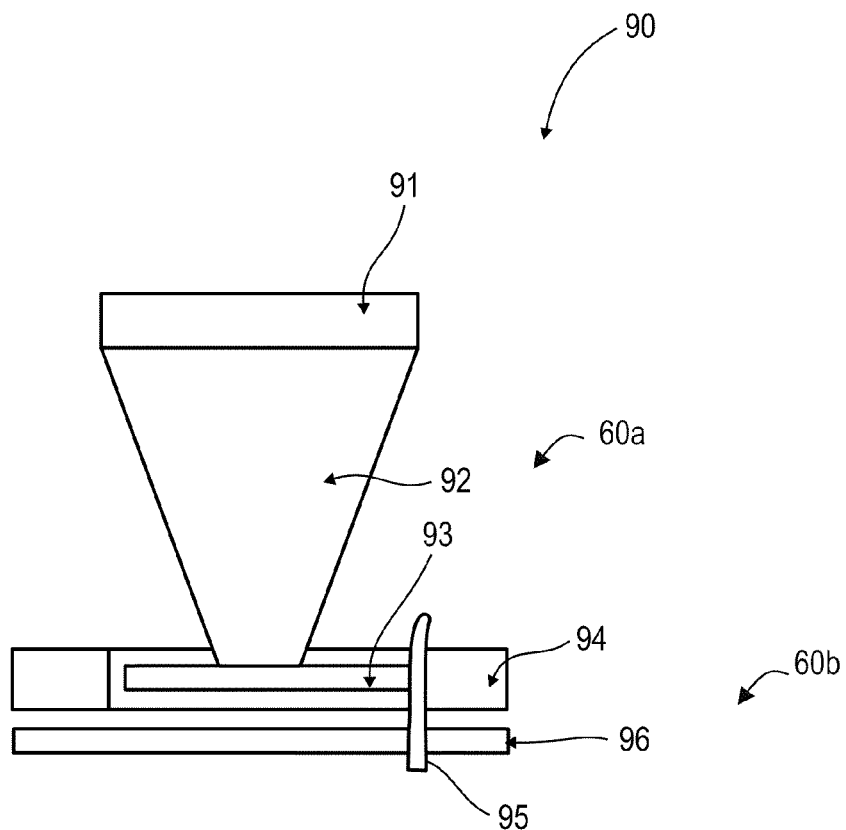
FIGS. 9A and 9B are a device for removing hair in embodiments of the invention in which the device comprises a vibrating element shaped as a disk and biasing unit having a ring which is configured to receives the vibrating element.
Figure 9B:
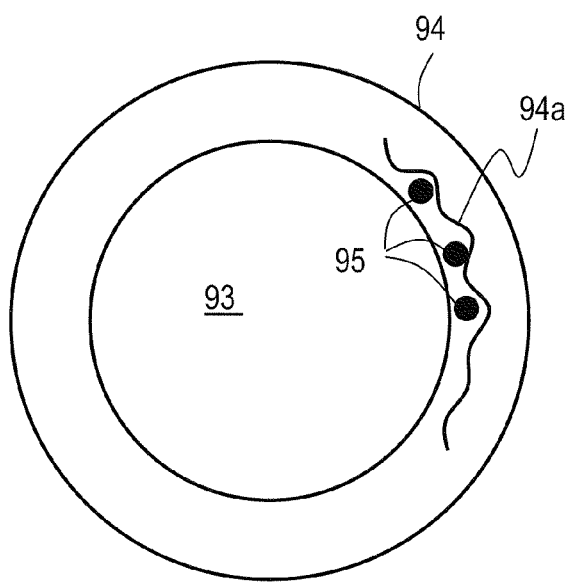

FIGS. 9A and 9B are schematic illustration of a device 90 for removing hair according to some embodiments of the present invention. Device 90 comprises a vibratory unit 90a serving as a "hammer" and a biasing unit 90b serving as an "anvil". Vibratory unit 90a includes an ultrasound transducer element 91, e.g., a piezoelectric element, a horn 92 and a vibrating element 93, which in the present embodiments is shaped as a disk. Horn 92 is constructed to receive vibrations from transducer element 91, and transmit the vibrations to vibrating element 93. Preferably, horn 92 is tapered toward vibrating element 93 so as to multiply the vibrations. In some embodiments, horn 92 is a stepped horn as known in the art.

Optionally and preferably, the amplitude of the vibrations are further amplified by the vibrating element 93. This can be done, for example, by providing vibrating element 93 with sufficient flexibility and elasticity such that the amplitude of the vibrations is enhanced by an elastic resonance effect. Thus, in various exemplary embodiments of the invention the amplitude of the vibratory displacement at the periphery of element 93 is X times larger than the amplitude of the vibratory displacement at the contact between horn 92 and element 93, where is can be any positive number larger than 1, as further detailed hereinabove.

Biasing unit 90b includes a ring 94 which may be formed with a plurality of inner teeth 94a as schematically illustrated in FIG. 9B. The inner diameter of ring 94 is selected such that ring 94 receives element 93 of unit 90a but allows for hair shafts 95 to enter the spacing between the outer periphery of element 93 and the inner periphery of ring 94. When ring 94 comprises teeth 94a, hair shafts 95 enter the spacing between the outer periphery of element 93 and teeth 94a and are grabbed by teeth 94a. In an alternative embodiment, the inner periphery of ring 94 is smooth but the outer periphery of element 93 is formed with teeth (not shown). In this embodiment, hair shafts 95 enter the spacing between the teeth of element 93 and the inner periphery of ring 94. Also contemplated are embodiments in which both the inner periphery of ring 94 and the outer periphery of element 93 are formed with teeth.

In various exemplary embodiments of the invention device 90 further comprises a hair raising mechanism 96 which can be similar to mechanism 76 as further detailed hereinabove.

In use, hair shafts 95 are lifted off the skin and enter the spacing between ring 94 and element 93 as described above. When element 91 is activated, vibrations are transmitted through horn 92 to vibrating element 93 which vibrates in a direction perpendicular to the plane of FIG. 9B. Element 93 transmits the vibrations to the hair shaft. These vibrations generate a longitudinal ultrasound wave in the hair shaft, which ultrasound wave generates heat at the root as further detailed hereinabove.

Transducer element 91 is preferably constructed so as to induce vibratory displacements of element 93 along the longitudinal axis of the hair, as shown by arrow 99a.

Figure 10:
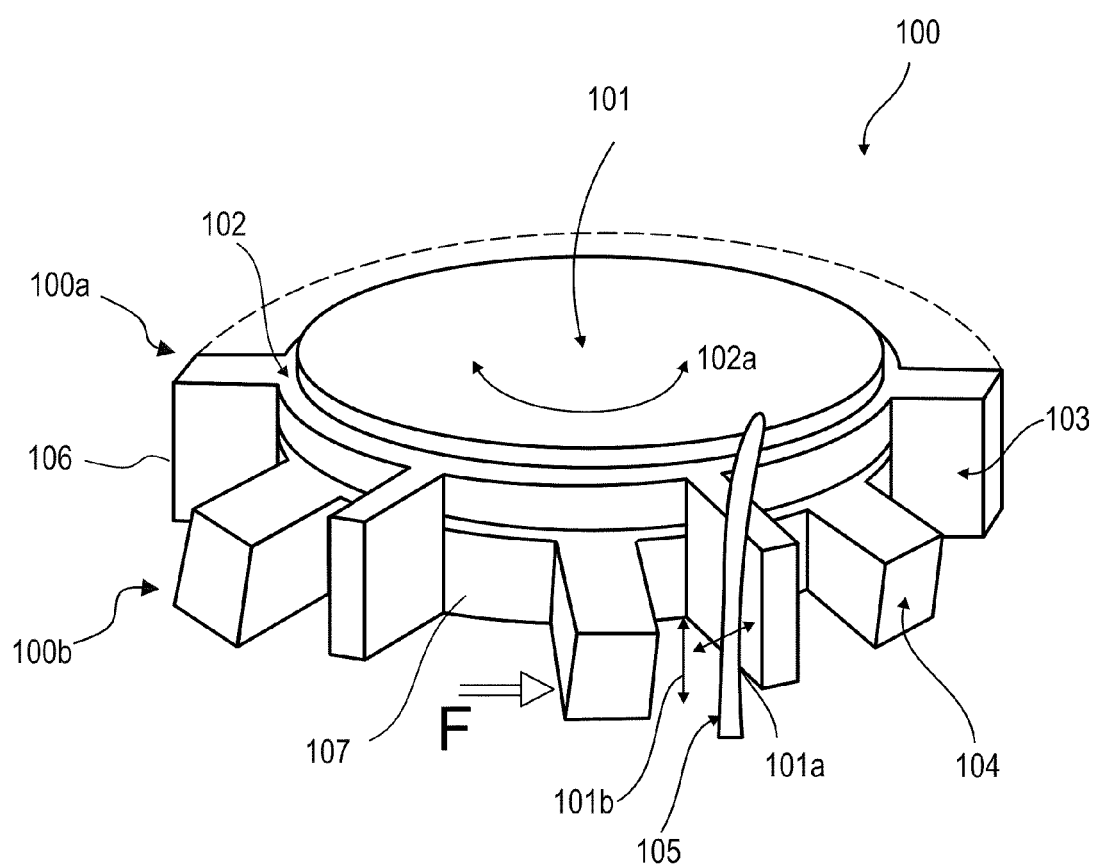
FIG. 10 is a schematic illustration of a device for removing hair in embodiments of the invention in which the device comprises a vibrating element which has the shape of a disk with a plurality of wings arranged on the periphery of the disk.

FIG. 10 is a schematic illustration of a device 100 for removing hair according to some embodiments of the present invention. Device 100 comprises vibratory unit 100a serving as a "hammer" and a biasing unit 100b serving as "an anvil".

Vibratory unit 100a comprises an ultrasound transducer element 101, e.g., a piezoelectric element, which is shown in FIG. 10 as a disk, but may also have other shapes. Vibratory unit 100a further comprises a vibrating element 106 which has the shape of a disk 102 with a plurality of wings 103 arranged on the periphery of disk 102. Wings 103 are generally planar and are perpendicular to the plane of disk 102. Transducer element 101 transfers vibrations to disk 102 either directly as shown in FIG. 10 or via an acoustic horn (not shown).

Biasing unit 100b is shape-wise compatible to vibrating element 106 of vibratory unit 100a. Specifically, biasing unit 100b has the shape of a disk 107 with a plurality of wings 104 arranged on the periphery of disk 107, wherein wings 104 of biasing unit 100b are interlaced with wings 103 of vibratory unit 100a.

Units 100a and 100b are mounted on each other in a manner that allows them to at least partially rotate one with respect to the other along a rotary direction indicated by an arrow 102a. Preferably, vibratory unit 100a and/or biasing unit 100b is rotatable such that device 100 can assume a position in which each of wings 103 is pressed against one of wings 104.

In use, hairs 105 are raised from the skin, e.g., by a raising mechanism (not shown) and are placed between wings 103 and 104. Unit 100a and/or unit 100b are rotated to grip the hairs between the wings and to apply a force F on the hair shafts 105. Transducer element 101 is energized and transfers vibrations to wings 103 via disk 102. The pressing force F between wings 103 and 104 which hold hair shaft 105 generates vibratory displacements of hair shafts 105 perpendicularly to the axis of the shaft as shown by arrow 101b, or along the axis of the shaft as shown by arrow 101a. This induces a longitudinal ultrasound wave along the axis of shaft 105, which ultrasound wave generates heat at the root of the hair as further detailed hereinabove.

Figure 11A:
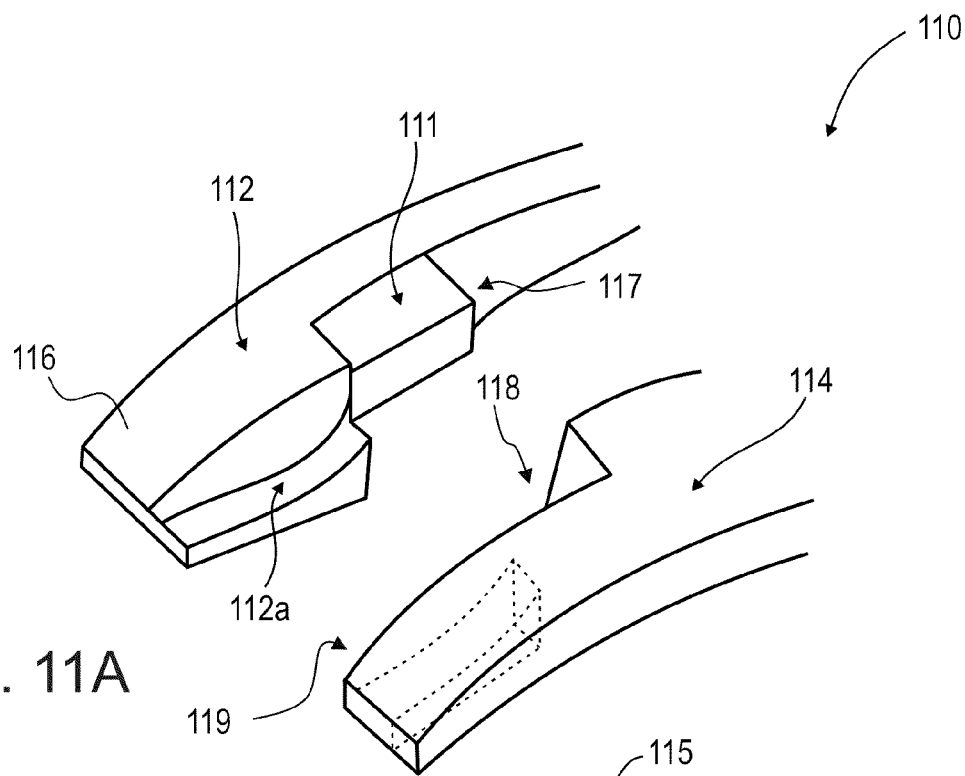
FIGS. 11A and 11B are schematic illustrations of a device for removing hair in embodiments of the invention in which the device comprises a bulge an outwardly protruding from tong and a compatible recesses formed in an opposite tong.
Figure 11B:
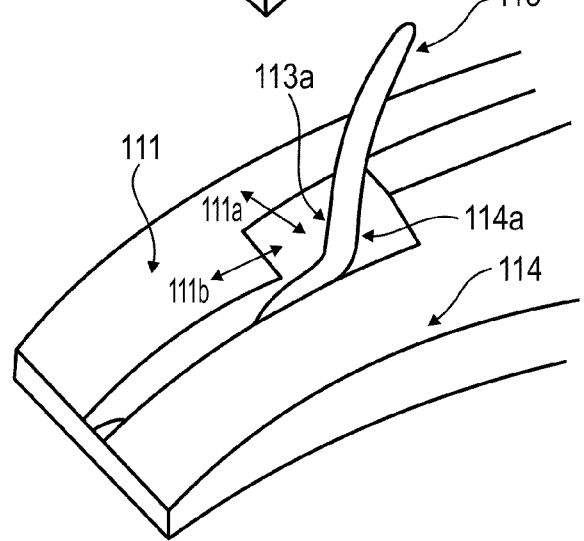

FIGS. 11A and 11B are schematic illustrations of a device 110 for removing hair according to some embodiments of the present invention. Device 110 comprises a vibratory unit or tong 112 and a biasing unit or tong 114. Vibratory tong 112 comprises a tong body 116 and a bulge 112a which is generally in the shape of a slanted surface outwardly protruding from body 116 of tong 112. Tong 112 is coupled to an ultrasound transducer element 111, e.g., a piezoelectric element, which may be positioned, for example, in a recess 117 formed in body 116.

Biasing tong 114 comprises a recess 119 which is shape-wise compatible to bulge 112a. Specifically, the shape and size of recess 119 are such that bulge 112a is fitted, preferably by its entirety, into recess 119. Second tong 114 may also comprise a second recess 118 which can be shaped to receive transducer element 111.

In use, the slanted surface of bulge 112a is slid under a hair shaft 115 and raises the hair shaft 115 from the skin. Tong 114 is then brought to engage tong 112 such that recess 119 of tong 114 receives bulge 112a and hair 115 is pressed between surface 113a of element 111 and surface 114a of tong 114. The engagement of tongs 112 and 114 can be such that part of hair shaft 115 protrudes outward from device 110, e.g., via second recess 118 of tong 114 as shown in FIG. 11B.

Transducer element 111 is energized and transfers vibrations directly to at least one of hair shaft 115, tong 112 and tong 114. The vibrations generate vibratory displacements in hair shaft 115 perpendicularly to the axis of the shaft as shown by arrows 101a and 101b. Transducer element 111 may also be constructed so as to generate vibratory displacements along the longitudinal axis of the hair. Also contemplated, are vibratory motions which are a combination of motion along the longitudinal axis of the hair and motion perpendicularly to the hair.

In any event, the vibratory displacements induce longitudinal ultrasound wave along the axis of shaft 115, which ultrasound wave generates heat at the root of the hair as further detailed hereinabove.

Figure 12:
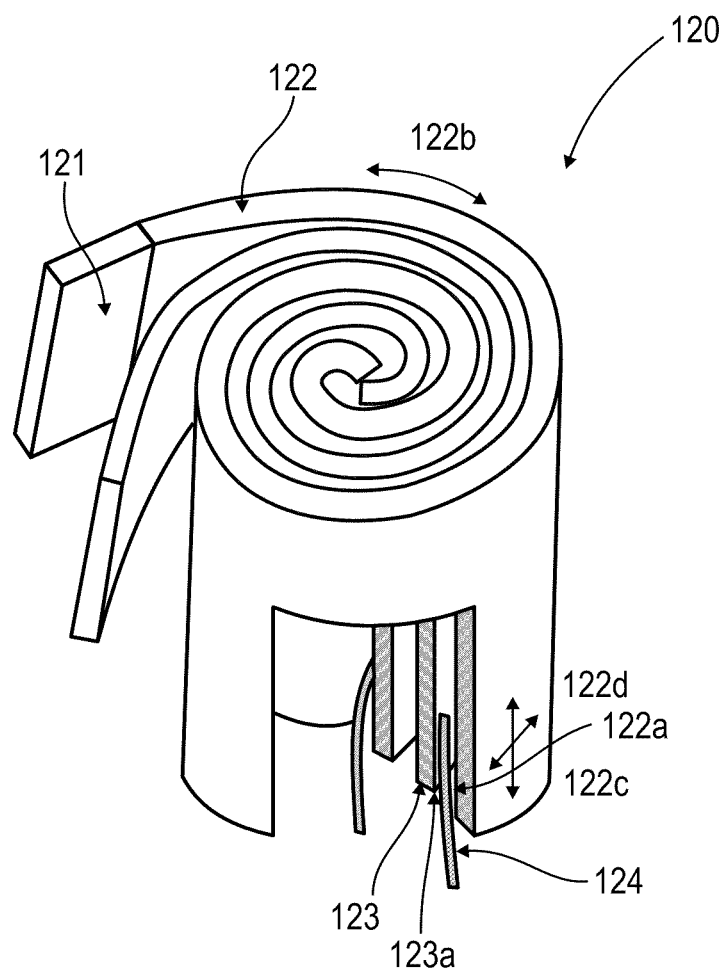
FIG. 12 is a schematic illustration of a device for removing hair in embodiments of the invention in which the device comprises sheets spirally wound one around the other.

FIG. 12 is a schematic illustration of a device 120 for removing hair according to some embodiments of the present invention. Device 120 comprises a vibratory unit 122 and a biasing unit 123, both being flexible, optionally and preferably elastic. Units 122 and 123 are shaped as sheets spirally wound one around the other.

Vibratory unit 122 comprises an ultrasound transducer element 121, e.g., a piezoelectric element, attached to or integrated with the flexible sheet. The flexibility of the sheet allows them to be tightened one onto the other along a rotary path generally indicated by arrow 122b. In use, hair shafts 124 are raised from the skin and introduced into the spacing between units 122 and 123. Thereafter, units 122 and 123 are tightened along direction 122b until hair shafts 124 are pressed between contact surface 123a of unit 123 and contact surface 122a of unit 122. Upon energizing of transducer element 121, vibrations are transferred to the flexible sheet of unit 122. The tightening between the sheets generates vibratory displacements of hair shafts 125 perpendicularly to the axis of the shaft, as shown by arrow 122d, or along the axis of the hair shafts as shown by arrow 122c. This induces a longitudinal ultrasound wave along the axis of the shaft, which ultrasound wave generates heat at the root of the hair as further detailed hereinabove.

Figure 13:
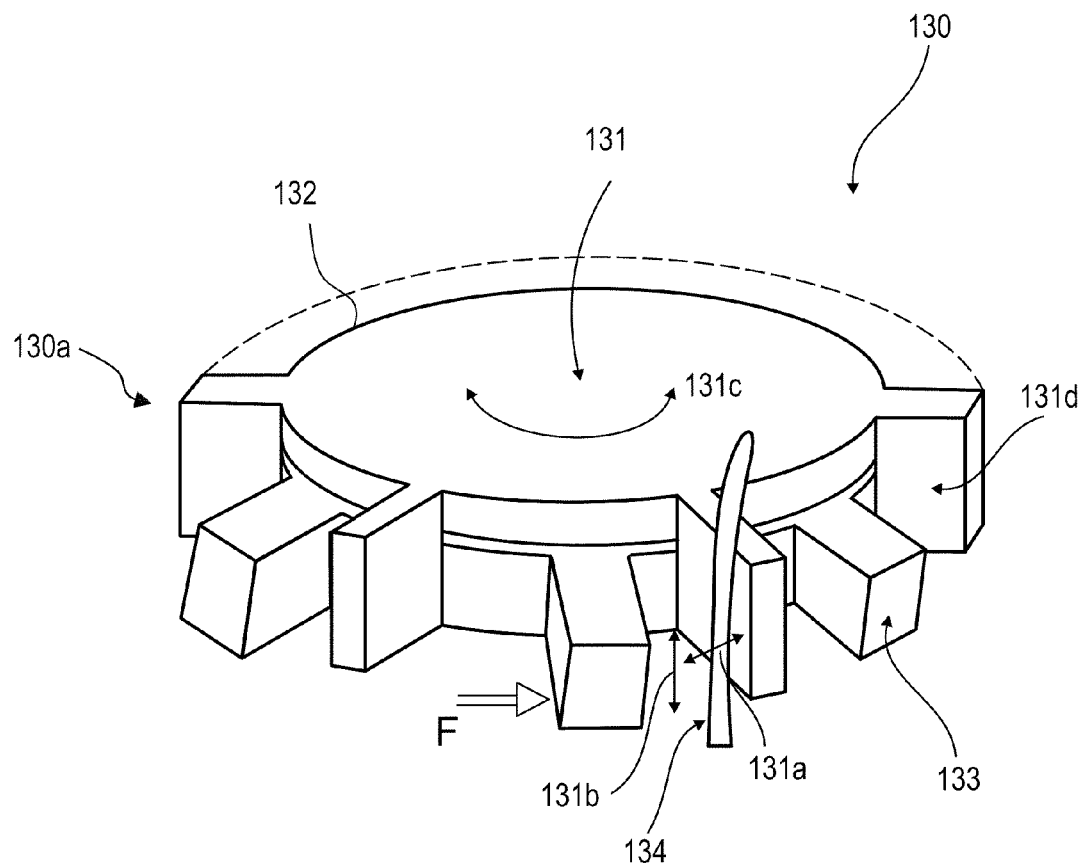
FIG. 13 is a schematic illustration of a device for removing hair in embodiments of the invention in which the device comprises an ultrasound transducer element shaped as a disk with a plurality of wings arranged on the periphery of the disk.

FIG. 13 is a schematic illustration of a device 130 which is a variant of device 100 in that in device 130 the transducer element is an integral part of the vibrating element. Hence, device 130 comprises an ultrasound transducer element 131, e.g., a piezoelectric element, which has the shape of a disk 132 with a plurality of wings 131 arranged on the periphery of disk 132. Transducer element 131 thus serves as a vibratory or hammer unit, designated 130a. Device 130 further comprises a biasing unit 133 which can be the same as the biasing unit 100b of device 10 described above.

The vibratory and biasing units are mounted on each other in a manner that allows them to at least partially rotate one with respect to the other along a rotary direction indicated by an arrow 131c. In use, hair shafts 134 are raised from the skin, e.g., by a raising mechanism (not shown) and are placed between the wings of the vibratory and biasing units as described above with respect to device 10. Transducer element 131 is energized and transfers the vibrations directly to hair shafts 134. This generates vibratory displacements of hair shafts 134 perpendicular to the axis of the shaft as shown by arrow 131b, or along the axis of the shaft as shown by arrow 131a, resulting in a longitudinal ultrasound wave along the axis of shaft 134. The ultrasound wave generates heat at the root of the hair as further detailed hereinabove.

Figure 14A:
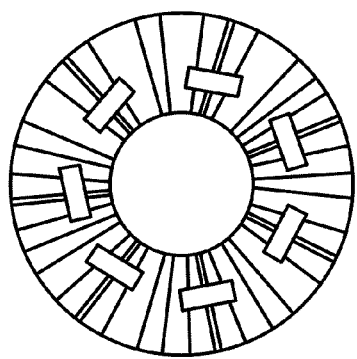
FIGS. 14A and 14B are schematic illustrations of a device for removing hair in embodiments of the invention in which the device comprises a plurality of vibratory units and a plurality of biasing units arranged alternately in a circular arrangement.
Figure 14B:
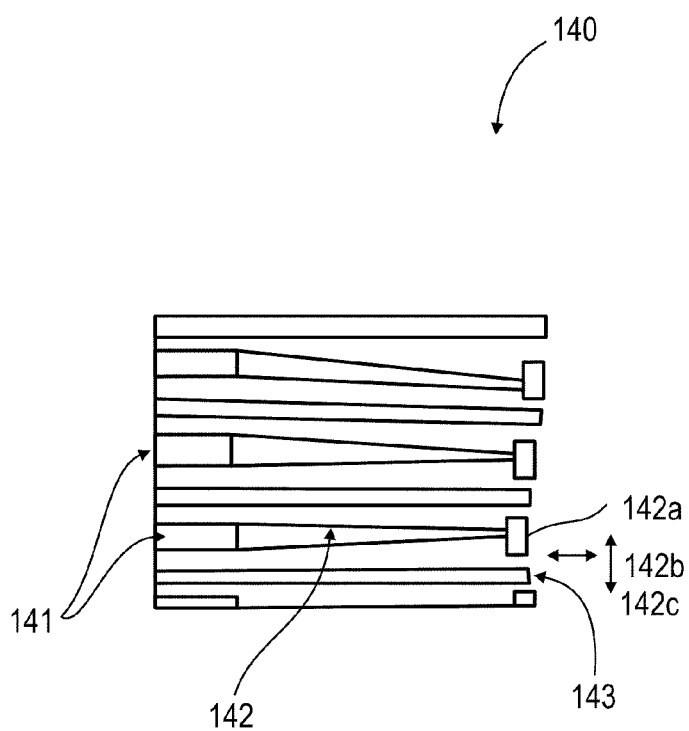

FIGS. 14A 14B illustrate a device 140 which is a variant of device 50 in that device 140 further comprises a plurality of vibratory units or tongs and a plurality of biasing units or tongs arranged alternately in a circular arrangement. Each vibratory tong comprises an ultrasound transducer element 141, e.g., a piezoelectric element, a horn 142 and a vibrating element 142a. Horn 142 is constructed to receive vibrations from transducer element 141, and transmit the vibrations to vibrating element 142a. Preferably, horn 142 is tapered toward vibrating element 142a so as to multiply the vibrations. In some embodiments, horn 142 is a stepped horn. The amplitude of the vibrations is preferably further amplified by vibrating element 142a, which in various exemplary embodiments of the invention is shaped as a hammer tip and is sufficiently elastic such that the amplitude of the vibrations is enhanced by an elastic resonance effect.

Thus, in various exemplary embodiments of the invention the amplitude of the vibratory displacement at the ends of element 142a are X times larger than the amplitude of the vibratory displacement at the contact between horn 142 and element 142a, where X is can be any positive number larger than 1, as further detailed hereinabove.

Each biasing tong 143 can be shaped according to any of the aforementioned embodiments. For example, biasing tongs 143 can be shapes as rods or planar surfaces.

In operation, vibrating elements 142a are pressed against biasing tongs 143 and the hairs (not shown) are gripped between them. Transducer element 141 may be constructed so as to induce vibratory displacements of element 142a along the longitudinal axis of the hair or perpendicularly thereto as shown by arrow 142b and 142c. This generates vibratory displacements of the hair shafts and result in a longitudinal ultrasound wave along the axis of shaft.

Figure 15A:
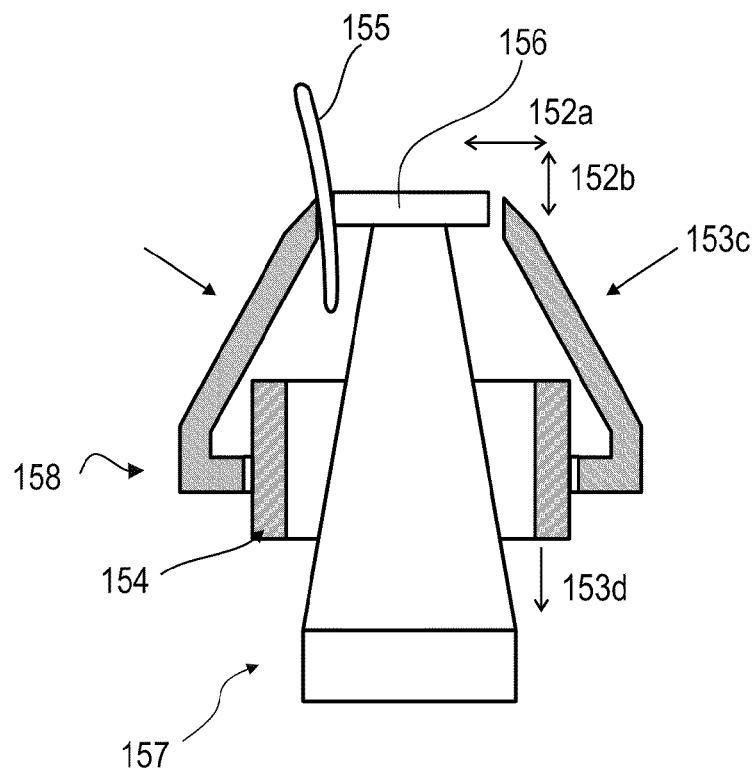
FIGS. 15A-15C are schematic illustrations of a device for removing hair in embodiments of the invention in which the device comprises a gripping element and an actuator mechanism for closing and opening the gripping element onto a vibrating element.
Figure 15B:
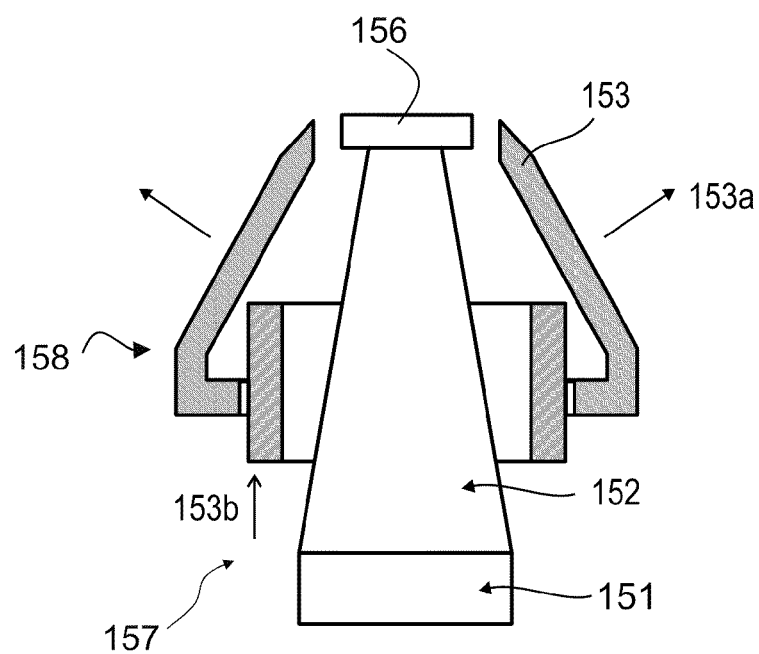
Figure 15C:
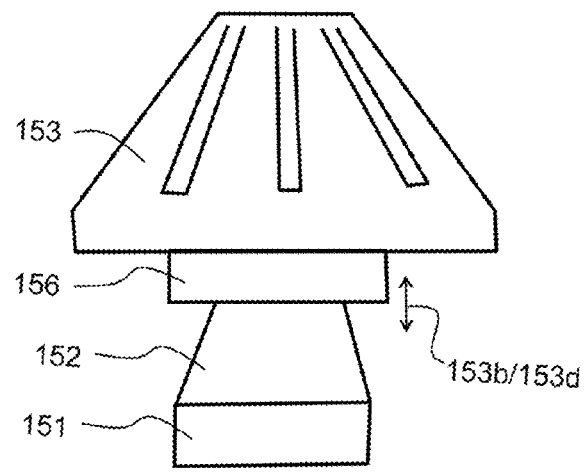

FIGS. 15A-C are schematic illustration of a device 150 for removing hair according to some embodiments of the present invention. Device 150 comprises a vibratory unit 157 serving as a "hammer" and a biasing unit 158 serving as "anvil". Vibratory unit 157 comprises an ultrasound transducer element 151, e.g., a piezoelectric element, a horn 152 and a vibrating element 156. Vibrating element 156 can be shaped, e.g., as a disk.

Preferably, horn 152 is tapered toward vibrating element 156 so as to multiply the vibrations. In some embodiments, horn 152 is a stepped horn as known in the art. Optionally and preferably, the amplitude of the vibrations are further amplified by the vibrating element 156. This can be done, for example, by providing vibrating element 156 with sufficient flexibility and elasticity such that the amplitude of the vibrations is enhanced by an elastic resonance effect. Thus, in various exemplary embodiments of the invention the amplitude of the vibratory displacement at the periphery of element 156 are X times larger than the amplitude of the vibratory displacement at the contact between horn 152 and element 156, where X is can be any positive number larger than 1, as further detailed hereinabove.

Biasing unit 158 comprises a gripping element 153 and an actuator mechanism 154 for closing and opening gripping element 153 onto vibrating element 156. Gripping element 153 can be shaped as a conical frustum as more clearly illustrated in FIG. 15C. In the embodiment illustrated in FIGS. 15A and 15B, actuator mechanism 154 is operative to establish a linear motion of gripping element 153 along horn 152. When gripping element 153 is brought 153d to assume a position closer to element 151 (FIG. 15A), gripping element 153 closes on vibrating element 156 and hair shafts 155 are gripped therebetween. When gripping element 153 is brought 153b to assume a position farther from element 151 (FIG. 15B), gripping element 153 is opened and there is no contact between vibrating element 156 and element 153. Gripping element 153 can be made elastic so as to more firmly grip the hair shafts when element 153 closes on element 156.

In use, hair shafts 155 are gripped between elements 153 and 156 and transducer element 151 is energized. Transducer element 151 may be constructed so as to induce vibratory displacements of element 156 along the longitudinal axis of the hair shafts or perpendicularly thereto as shown by arrow 152b and 152a. This generates vibratory displacements of the hair shafts and result in a longitudinal ultrasound wave along the axis of shaft.

In embodiments in which a longitudinal ultrasound wave is generated in the hair shaft by direct vibration, the transducer element preferably vibrates at an ultrasound frequency of from about 100 kHz to about 500 kHz. The mechanical vibration at the contact between the hair shafts and the vibrating element are preferably at amplitude of from about 5 μm to about 50 μm.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for removing hair, comprising:
a vibratory unit having an ultrasound transducer element, a vibrating element and an acoustic horn between said transducer element and said vibrating element, wherein vibratory motion of said transducer element is transferred by said horn to said vibrating element; and
a biasing unit having a gripping element and an actuator mechanism configured for closing and opening said gripping element onto said vibrating element,
said actuator mechanism being operative to establish a linear motion of said gripping element along said horn such that a linear motion along a first direction opens a gap between said gripping element and said vibrating element to receive hair shafts in said gap, and a linear motion along a second direction, opposite to said first direction, closes said gripping element on said vibrating element so as to grip said hairs therebetween and to transfer said vibratory motion to said hair shafts for generating ultrasound wave therein.

2. The device according to claim 1, further comprising a hair raising mechanism configured for raising said hair shafts from a skin of a subject to facilitate entry of said hair shafts to the device.

3. The device of claim 1, wherein said ultrasound waves are at a frequency of from about 100 kHz to about 500 kHz.

4. The device of claim 1, wherein mechanical vibration at the contact between the hair shafts and the vibrating element are at amplitude of from about 5 µm to about 50 µm.

* * * * *